United States Patent
Barringer, Jr.

(10) Patent No.: US 7,169,599 B2
(45) Date of Patent: Jan. 30, 2007

(54) FLUID INTERFACE FOR BIOPROCESSOR SYSTEMS

(75) Inventor: George E. Barringer, Jr., West Groton, MA (US)

(73) Assignee: Groton Biosystems, LLC, Acton, MA (US)

( * ) Notice: Subject to any disclaimer, the term of this patent is extended or adjusted under 35 U.S.C. 154(b) by 479 days.

(21) Appl. No.: 10/601,083

(22) Filed: Jun. 20, 2003

(65) Prior Publication Data

US 2004/0259241 A1 Dec. 23, 2004

(51) Int. Cl.
*C12M 1/36* (2006.01)
*C12M 1/38* (2006.01)
*C12M 3/00* (2006.01)
*C12M 1/26* (2006.01)
*G01N 1/20* (2006.01)

(52) U.S. Cl. ............... 435/286.5; 435/309.2; 435/3; 435/30; 73/863.71; 73/864

(58) Field of Classification Search ............... 422/103; 73/863.86
See application file for complete search history.

(56) References Cited

U.S. PATENT DOCUMENTS 4,167,117 A * 9/1979 Stokley et al. ........... 73/863.58
4,785,676 A  11/1988 DeOca et al.

(Continued)

FOREIGN PATENT DOCUMENTS

EP  0443320  8/1991

(Continued)

OTHER PUBLICATIONS

Arce, L, et al., "On-line Ion-exchange Preconcentration in a Flow Injection System Coupled to Capillary Electrophoresis for the Direct Determination of UV Absorbing Anions," *Analytica Chimica Acta*, 390: 39-44 (1999).
Burgi, D. S. and Chien R., "Optimization in Sample Stacking for High-Performance Capillary Electrophoresis," *Analytical Chemistry*, 63(18): 2042-2047 (1991).

(Continued)

*Primary Examiner*—Gladys J P Corcoran
*Assistant Examiner*—Nathan Bowers
(74) *Attorney, Agent, or Firm*—Hamilton, Brook, Smith & Reynolds, P.C.

(57) ABSTRACT

An apparatus and method for an aseptic fluidic interface between bioprocess systems is provided. The apparatus includes an inlet valve, adapted for automatic control, that is coupled to a biofluid source site. A sampling conduit extends from the inlet valve to an outlet valve. The outlet valve is adapted for automatic control and is coupled to a biofluid process site. A trap is at the sampling conduit. A waste valve, adapted for automatic control, is located at a waste conduit extending from the sampling conduit to a waste site. Also included is a wash fluid source that is coupled to at least one of the inlet or outlet valves. In the method, the sample is automatically directed to the biofluid process site by opening the outlet valve, and closing the waste valve Also included is isolating the biofluid sites by closing the inlet and outlet valves, and opening the waste valve to drain biofluid from the trap to the waste site. Another step is cleaning the sampling conduit before sample collection by directing the wash fluid through at least one valve selected from the inlet and outlet valves, and subsequently through the waste valve to the waste site.

24 Claims, 25 Drawing Sheets

U.S. PATENT DOCUMENTS

| | | | |
|---|---|---|---|
| 4,942,770 | A | 7/1990 | Seifert et al. |
| 4,999,307 | A | 3/1991 | Oakley |
| 5,075,905 | A * | 12/1991 | Rutherford ............. 137/247.51 |
| 5,296,197 | A | 3/1994 | Newberg et al. |
| 5,372,695 | A | 12/1994 | Demorest |
| 5,395,588 | A * | 3/1995 | North et al. .................. 422/81 |
| 5,429,728 | A | 7/1995 | Gordon |
| 5,460,054 | A * | 10/1995 | Tran ........................ 73/863.61 |
| 5,482,608 | A | 1/1996 | Keely et al. |
| 5,755,155 | A | 5/1998 | Buesing |
| 5,771,917 | A | 6/1998 | Carney et al. |
| 5,833,826 | A | 11/1998 | Nordman |
| 5,902,746 | A | 5/1999 | Colin et al. |
| 5,948,998 | A | 9/1999 | Witte et al. |
| 5,985,121 | A | 11/1999 | Wu et al. |
| 6,254,060 | B1 * | 7/2001 | Kennedy .................... 251/197 |
| 6,375,855 | B1 | 4/2002 | Vassarotti |
| 6,418,799 | B1 | 7/2002 | Pardue et al. |
| RE37,941 | E | 12/2002 | Guttman |
| 6,491,804 | B2 | 12/2002 | Manz et al. |
| 6,491,872 | B1 | 12/2002 | Wick |
| 6,537,432 | B1 | 3/2003 | Schneider et al. |
| 2001/0005489 | A1 | 6/2001 | Roach et al. |
| 2002/0170364 | A1 * | 11/2002 | Gerard et al. ............ 73/863.86 |

FOREIGN PATENT DOCUMENTS

| | | |
|---|---|---|
| EP | 0 566 645 B1 | 10/1994 |
| EP | 0 607 234 B1 | 5/1995 |
| WO | WO 93/06741 | 4/1993 |

OTHER PUBLICATIONS

Bleha, M, et al., "Role of Convection in Dialysis Desalination of Protein Mixtures by Microporous Charged Neosepta Membranes," *Membrane*: 21(2): 144-152 (1996).

Chen, H and Fang, Z, "Combination of Flow Injection with Capillary Electrophoresis. Part 3. On-line Sorption Column Preconcentration Capillary Electrophoresis System," *Analytica Chimica Acta*: 355: 135-143 (1997).

Chien, R. and Burgi, D. S., "Sample Stacking of an Extremely Large Injection Volume in High-Performance Capillary Eletrophoresis," *Analytical Chemistry*, 64(9): 1046-1050 (1992).

Jiang, Z., et al., "Separation of Pyridazinone Derivatives Using Pressurized Gradient Capillary Electrochromatography," *J. Microcolumn Separations*: 13(5) 191-196 (2001).

Jin, H., et al., "Purification and Renaturation of Recombinant Human Lymphotoxin (Tumour Necrosis Factor Beta) Expressed in *Escherichia coli* as Inclusion Bodies," *J. Chem. Tech. Biotechnol.*, 59: 67-72 (1994).

Kaul, R. and Mattiasson, B, "Secondary Purification," *Bioseparation*, 3: 1-26 (1992).

Kuban, P., et al., "New Interface for Coupling Flow-injection and Capillary Electrophoresis," *Analytica Chimica Acta*, 337: 117-124 (1997).

Lacoste, B., et al., "Study of an Aerobic Concentrated Culture Reactor Coupled to Separation by Crossflow Micro- or Ultrafiltration Through Inorganic Membranes. Initial Approach to a Depollution Application," *Revue Des Sciences De L'eau*, 6(4): 363-380 (1993).

Masi, C. G., "Choosing Automation for Fast Liquid Sample Handling," *Drug Discovery & Development*, Jan. issue: 36-41 (2003).

Seifert, G. K. E. and Matteau, P. P., "An Automatic Aseptic Bioreactor Sampling System," *Biotechnology and Bioengineering*, 32: 923-926 (1988).

Shihabi, Z., "Stacking in Capillary Zone Electrophoresis," *Journal of Chromatography A*, 902: 107-117 (2000).

Sinacola, J. R. and Robinson, A.S., "Rapid Refolding and Polishing of Single-chain Antibodies from *Escherichia coli* Inclusion Bodies," *Protein Expression & Purification*, 26: 301-308 (2002).

Tishchenko, G., et al., "Separation of Specific Immunoglobulin. 1. Desalination Using a Membrane System," *Bioseparation*, 5: 19-25 (1995).

* cited by examiner

FLUID INTERFACE FOR BIOPROCESSOR SYSTEMS

BACKGROUND OF THE INVENTION

Analysis of macromolecules in complex mixtures is challenging in many chemical and biochemical processes. For example, the analysis of a macromolecule product, e.g., a protein, typically involves first preparing a sample of a macromolecule from a complex mixture for analysis. FIG. 1 depicts an example of a macromolecule preparation process 100, which involves taking a sample from a complex liquid mixture, e.g. a biofluid in a bioreactor 102, separating a macromolecule 104 from other components in the mixture, and processing it to deliver a prepared macromolecule 104' for analysis at analyzer 106.

Effective process control generally requires accurate and frequent sampling, yet sampling of an operating bioreactor is associated with numerous problems, particularly contamination from sampling. For example, a bioreactor fluid typically contains, in addition to the macromolecule of interest, components such as salts, nutrients, proteins, peptides, cells, cell components, biopolymers such as polysaccharides, and the like, all of which can confound analysis of the desired products. Sampling can introduce, for example, foreign or wild bacteria into a bioreactor, which can compete with the process bacteria in the bioreactor fluid. Other contaminants, e.g., chemical contaminants, can affect the growth of the process bacteria and can confound the analysis of process components in the bioreactor fluid. Contamination can also affect the sampling and analysis apparatus. For example, wild or process bacteria can colonize the sampling/analysis system, or the system can accumulate other components form the biofluid, e.g., as salts, nutrients, proteins, peptides, cells, cell components, biopolymers such as polysaccharides, all of which can confound analysis of the desired products. Additionally, frequent sampling can lead to build-up of the molecule or molecules being analyzed, which can lead to inaccuracy.

In particular, the problem of "backflow", i.e., liquid cross-contamination, is especially difficult when interfacing two fluidic systems. Simple valve interfaces are inadequate because valves typically have crevices, joints, dead volume, and the like, where contaminants can lodge and accumulate, only to be released during another sample cycle. Additionally, valves can fail and allow undesirable contamination to occur before much measurable fluid has leaked. More complex valved interfaces are known, but some are costly and still suffer some of the problems of simple valve systems, while other examples are unsuitable for high pressure systems. Needle/septa interfaces are known to avoid backflow but have issues with septa lifetime, needle contamination during transfer, and are particularly troublesome for frequent, automated sampling of larger volumes. Furthermore, septa replacement itself opens the system for contamination.

FIG. 2 depicts typical steps that can be included in a macromolecule sample preparation process operating on a mixture 202. If the macromolecule is endogenous, i.e., is at least partly contained in cells, an optional lysing step 204 opens the cells so that the macromolecule 104 can be separated. Separation step 206 separates macromolecule 104 from rough components 207 and fine components 213. Rough components 207 can include, for example, insoluble cells 208, cellular fragments 210, soluble molecules 212 which are larger than macromolecule 104, and the like. Fine components 213 can include salts 214 and soluble molecules 215 that are smaller than macromolecule 104, and the like. The concentration of ions such as salts and hydrogen (i.e., pH) are adjusted in step 216. In step 218, the molecule can be denatured, i.e., can be heated and/or combined with a denaturing agent 220, producing prepared macromolecule 104', which is typically at an increased concentration compared to macromolecule 104.

The various steps used for protein preparation in the prior art involve separation of components through labor intensive centrifugation or time-intensive matrix chromatography. Matrix chromatography uses expensive columns that can be prone to plugging when used with complex mixtures that include insoluble or precipitation-prone components. Centrifugation can be effective but can cause contamination problems as there is no way to readily isolate a sample from the environment during the various sample transfers typically employed, and the size of the centrifuge limits the amount of macromolecule that can be prepared at one time. Thus both methods are low throughput in terms of amount of macromolecule that can be prepared.

Additionally, both methods are low throughput in terms of the sampling frequency, as the time from sample extraction from a complex bioreactor mixture to analysis of the macromolecule can easily be four hours or more. Such a slow analysis time leads to poor optimization of reactor processes, resulting in lowered yields, increased costs, increased purification demands, and increased amounts of potentially hazardous biological waste. FIG. 3 depicts a hypothetical example comparing two sampling frequencies, wherein a lower sampling frequency versus time (squares) can miss details in the level of a desired macromolecule versus time (solid line) in a reaction mixture, compared to a higher sampling frequency (circles). For example, the lower sampling frequency can miss the maximum macromolecular concentration 302 by measuring only lower concentration 300.

Electrophoresis is an analytical technique commonly used to separate molecular species, e.g., peptides, proteins, oligonucleotides, small organic molecules, and the like. The molecules, in a separation medium, e.g., a solution or a gel matrix, separate under an applied electric field according to their electrophoretic mobility, which is related to the charge on each molecule, its size, and the viscosity of the separation medium.

FIG. 10 depicts the separation of a small molecule 1002 and a large molecule 1004, each with the same net positive charge, and a small negatively charged molecule 1006. Application of electric field 1008 causes differential motion of the charged molecules according to their electrophoretic mobilities, with cations 1002 and 1004 moving towards the anode 1010. In the ideal case, the anions 1006 move to the cathode 1012, though experimentally a phenomenon known as electroosmotic flow can reduce or reverse the anion to cathode motion.

In capillary electrophoresis (CE), the separation is performed in a capillary tube having an internal diameter on the order of tens to hundreds of micrometers. In such small tubes the heat generated by the electric field is easily dissipated, so that high electrical fields can be used, leading to fast separations. FIG. 11 depicts a schematic of an electrophoresis apparatus 1100. An inlet vessel 1102 and an outlet vessel 1104 are connected by a capillary column 1106. The vessels and the capillary contain a buffer with an appropriate electrolyte. Upon loading a sample containing the analyte of interest at the inlet vessel, an electric field provided by a high voltage power supply 1108 causes the various molecules in the sample to separate, whereupon they can be detected by a detector 1110.

While capillary electrophoresis is powerful and versatile, it is sensitive to variations in acidity (pH), ionic strength, temperature, viscosity and other physical characteristics of the mixture, properties intrinsic to the analytes being studied, and contamination issues. Furthermore, small capillaries are physically fragile and are not suited to high-throughput separations, being easily plugged from the many macromolecules and debris in a complex mixture. In particular, rapid separation and analysis of macromolecules from complex liquid mixtures, for example, during the analysis of proteins produced in a bioreactor, is especially challenging.

In one example of CE technology a fragile, small diameter capillary is repeatedly applied by robotics to a series of distinct inlet vials. The repetitive motion can easily break the CE column. Column replacement requires time-consuming recalibration of the robotic motion. Another example of CE technology employs microchannels etched into a glass chip. While this hardware is durable, the separation efficiency is limited by the length of CE channel that can be fabricated on a chip. Attempts to extend the channel length by increasing channel density on a chip generally restrict high electric fields from use, increasing separation time. Also, the throughput of this technique is limited. Furthermore, sample transfer as practiced in both the robotic capillary technique and the chip technique expose the analytic solution to undesirable environmental contamination.

SUMMARY OF THE INVENTION

A method and apparatus for an aseptic fluidic interface between bioprocess systems is provided. In particular applications, methods and apparatus are provided for aseptically sampling a biofluid from a bioreactor and directing the sample to a macromolecule polishing and analysis site.

An apparatus is an aseptic fluidic interface between bioprocess systems. The apparatus includes an inlet valve, adapted for automatic control, that is coupled to a biofluid source site. A sampling conduit extends from the inlet valve to an outlet valve. The outlet valve is adapted for automatic control and is coupled to a biofluid process site. A trap is located at the sampling conduit. A waste valve, adapted for automatic control, is located at a waste conduit extending from the sampling conduit to a waste site. Also included is a wash fluid source that is coupled to at least one of the inlet or outlet valves.

A method of aseptically sampling a biofluid with the apparatus includes automatically collecting a biofluid sample by opening the inlet valve. The sample is automatically directed to the biofluid process site by opening the outlet valve, and closing the waste valve. Another step is isolating the biofluid sites by closing the inlet and outlet valves, and opening the waste valve to drain biofluid from the trap to the waste site. Another step is cleaning the sampling conduit before sample collection by directing the wash fluid through at least one valve selected from the inlet and outlet valves, and subsequently through the waste valve to the waste site.

The methods and apparatus disclosed herein provide significant advantages to aseptically sampling a biofluid and directing it to a bioprocess site. The valve and conduit system excludes environmental contamination and facilitates rapid, frequent, automated sampling. The trap allows the use of simple valves yet avoids the problems associated with valve deadspace. Furthermore, the trap provides the ability to detect flow, e.g. from a failing valve, before backflow or cross-contamination occurs. Additionally, the valved, automated system coupled to a wash fluid source and a waste site allows the system to be thoroughly cleaned between sample cycles, thus assuring contamination-free sampling. The result is improved sampling accuracy and frequency for improved control and lower cost in bioprocess systems.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The methods and apparatus disclosed herein are generally related to analyzing a sample of a molecular analyte, e.g., a macromolecule, from a complex liquid mixture. The invention has particular application to automated methods and apparatus for capillary electrophoretic analysis macromolecules, e.g., proteins, from a complex bioreactor liquid mixture.

Automated Macromolecule Preparation

Figure 1:
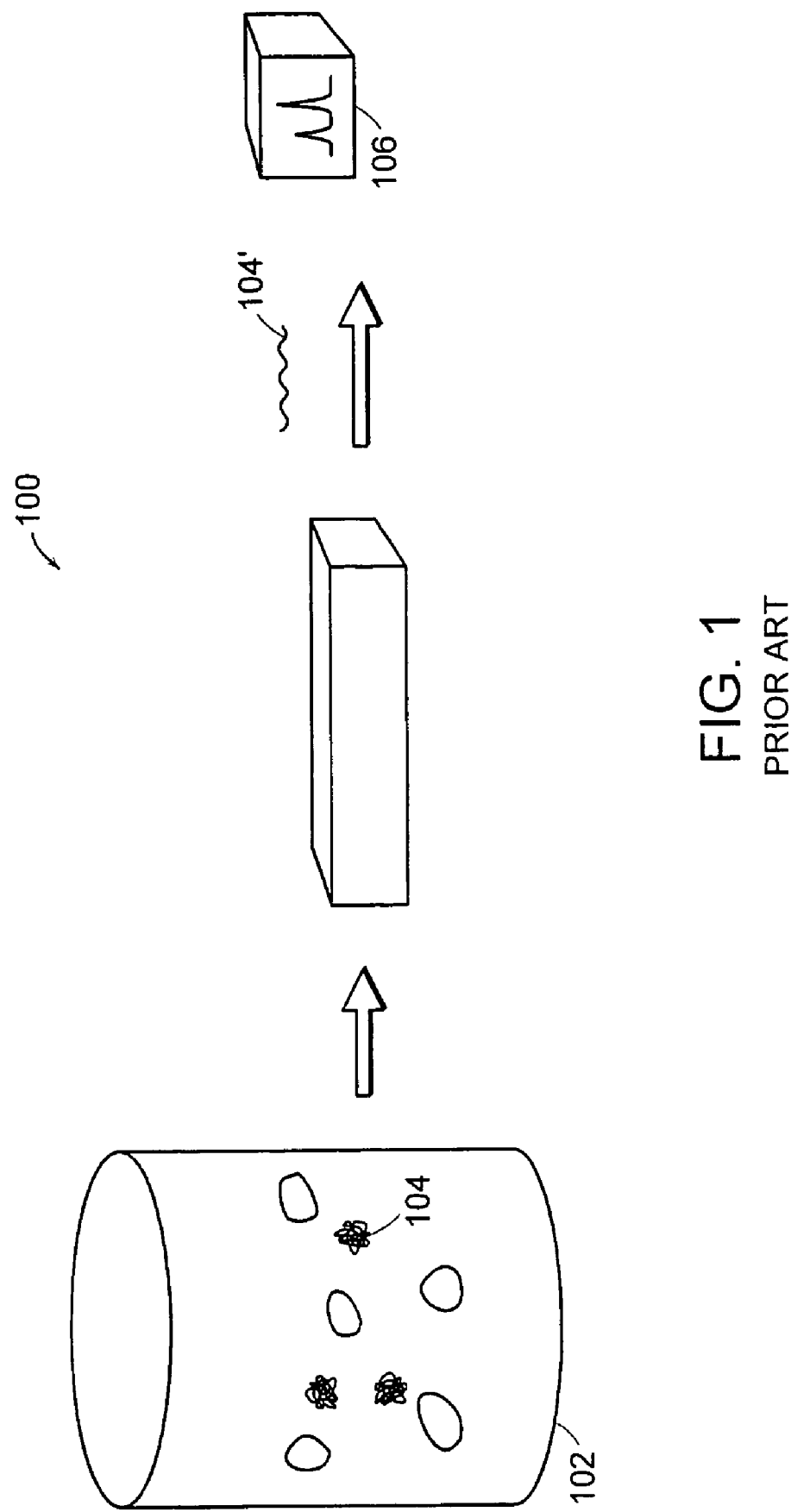
FIG. 1 depicts an example of a macromolecule preparation apparatus 100.
Figure 2:
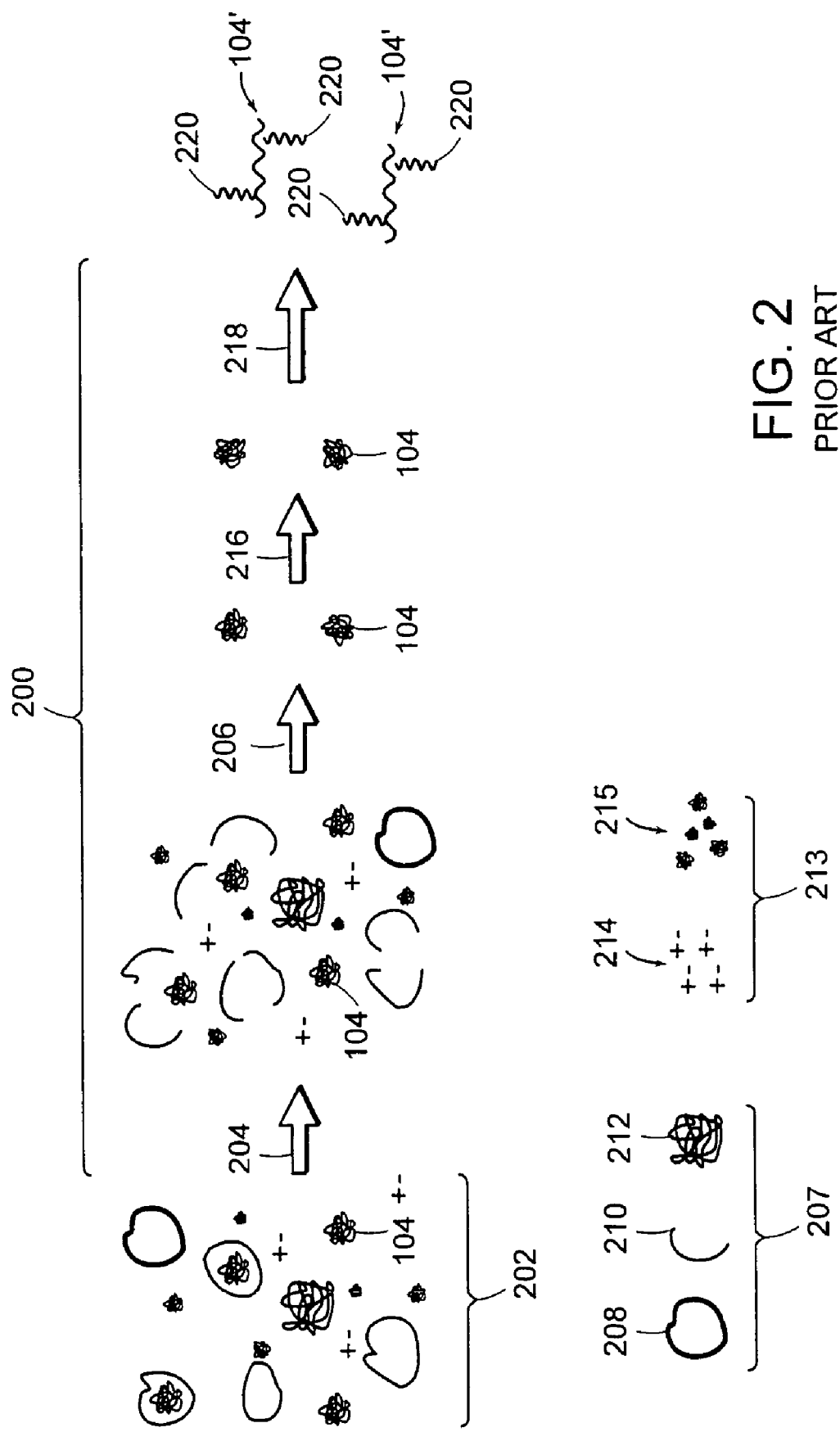
FIG. 2 depicts typical steps that can be included in a macromolecule sample preparation process 200 operating on a mixture 202.
Figure 3:
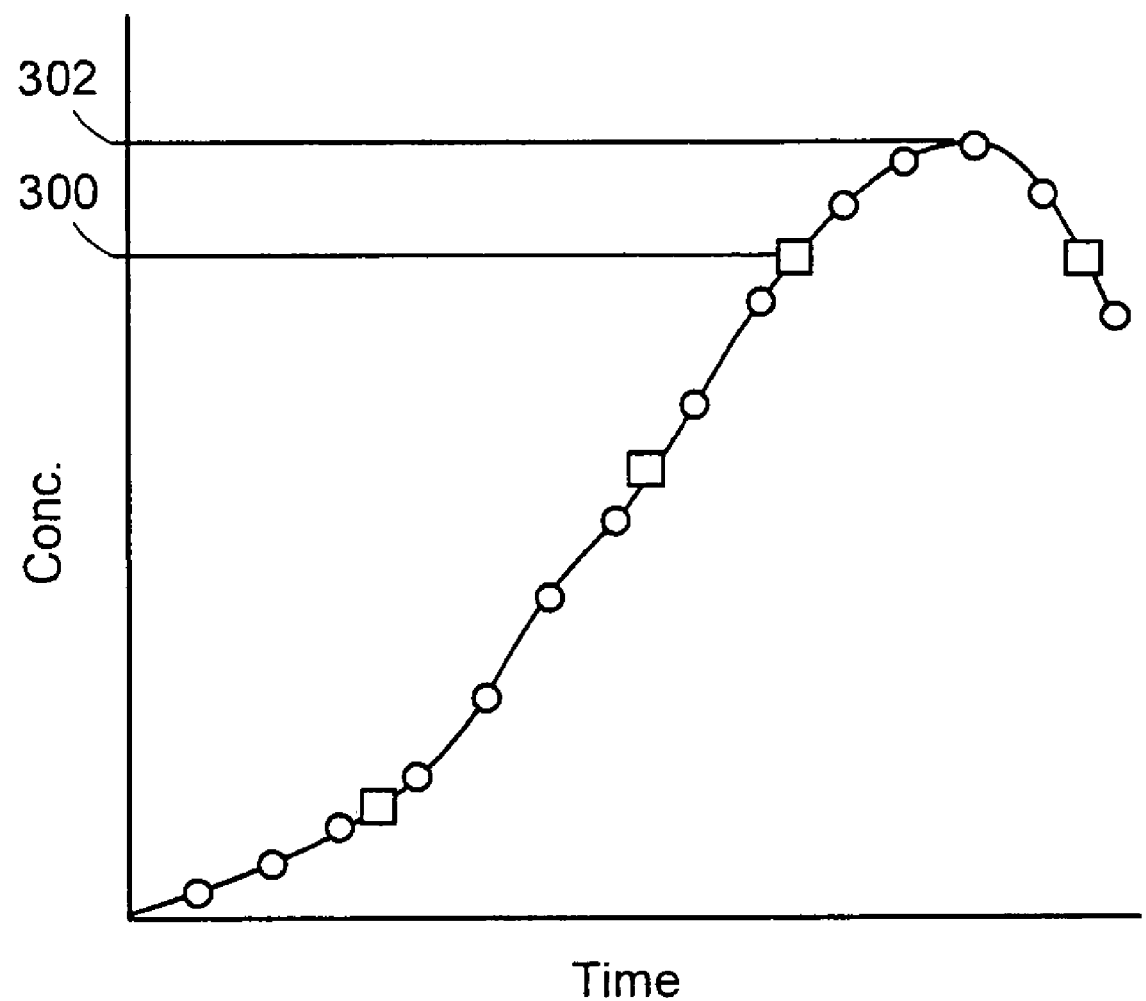
FIG. 3 depicts a hypothetical example comparing two sampling frequencies, wherein a lower sampling frequency versus time (squares) can miss details in the level of a desired macromolecule versus time (solid line) in a reaction mixture, compared to a higher sampling frequency (circles).
Figure 4:
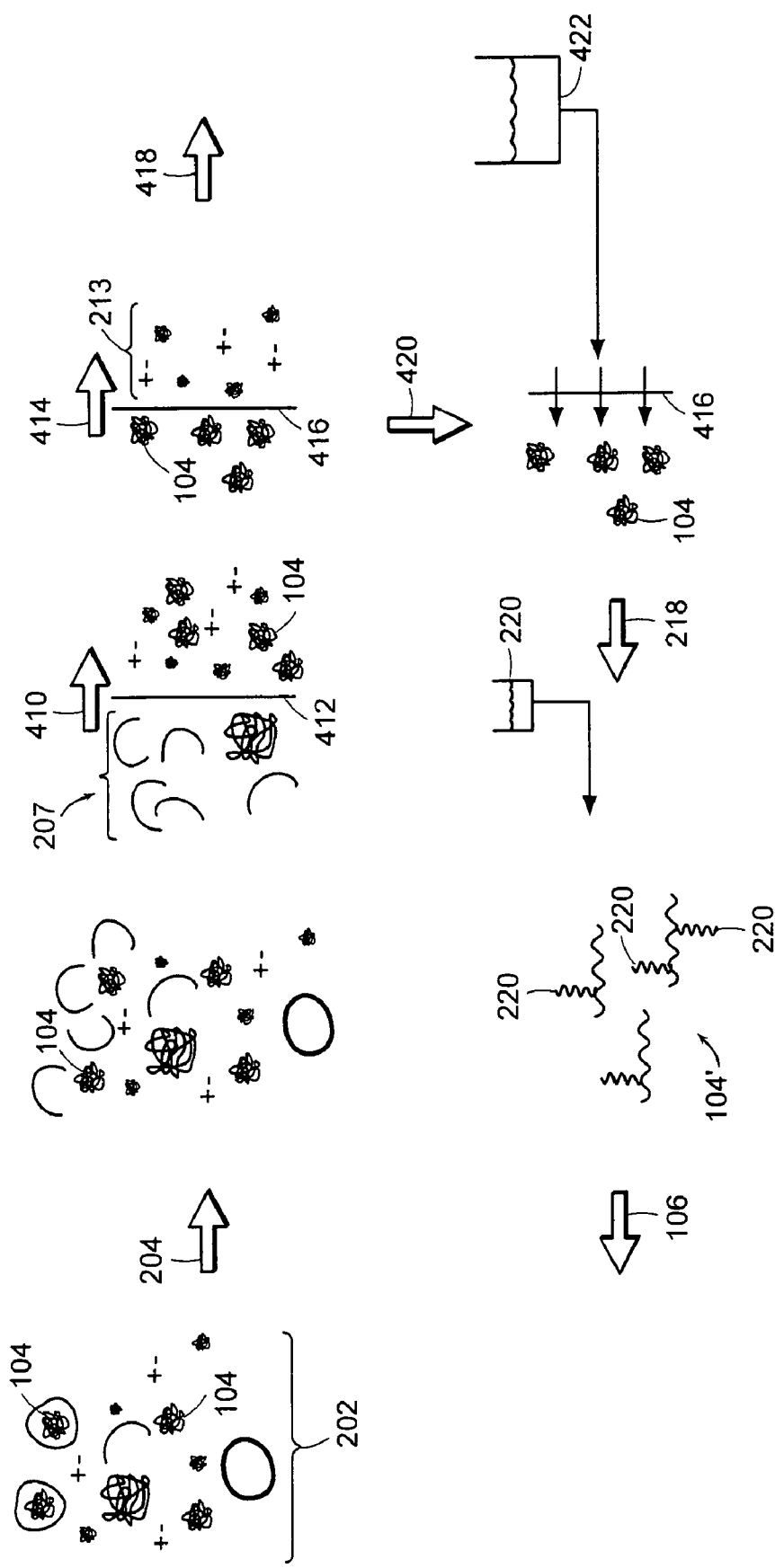
FIG. 4 depicts a schematic of steps that can be included in preparing a macromolecule sample.

FIG. 4 depicts a schematic of steps that can be included in preparing a macromolecule sample. The liquid, typically aqueous, mixture 202 contains the macromolecule 104, and can also contain fine components 213, e.g., salts, molecules smaller than the macromolecule, and the like; and rough components 207, e.g., cells, cell fragments, particulate contaminants, molecules larger than the macromolecule, and the like.

Macromolecule 104 can be dissolved in the liquid mixture, or can be partially contained in cells, as depicted. Optional lysis step 204 lyses at least a portion of the cells to release macromolecule 104. Lysing can be conducted using any method of lysing cells well-know to the art, for example, heating, sonic disruption, addition of lysing agents, e.g., detergents, changes in ionic strength, e.g., by dilution with water or combination with a lysis buffer, and the like.

A rough separation step 410 applies the liquid mixture to a rough filter 412, and a pressure differential across filter 412 directs at least a portion of the liquid, macromolecule 104, and the fine components 213 through the filter, separating at least a portion of rough components 207 at rough filter 412. Rough filter 412 can be selected to remove at least a portion of components that are larger than the macromolecule, e.g., greater in diameter or molecular weight. Preferably, rough filter 412 removes components that are greater in molecular weight than the molecular weight of the macromolecule by about 150%, more preferably about 125%, even more preferably about 110%, and most preferably, about 105%. In other aspects, rough filter 412 can be selected to remove at least a portion of components that are greater in diameter than about 60 µm, more preferably about 30 µm, even more preferably about 10 µm, or most preferably about 5 µm.

A fine separation step 414 applies the liquid mixture to a fine filter 416, and a pressure differential across the filter directs at least a portion of the liquid and the fine components 213 through the filter to waste 418, separating at least a portion of macromolecule 104 at the filter. Fine filter 416 can be preferably selected to remove at least a portion of components that are smaller than the macromolecule, e.g., salt components. Preferably, the fine filter removes components that have a molecular weight that is a fraction of the molecular weight of macromolecule 104 of preferably about 50%, more preferably about 75%, even more preferably about 90%, and most preferably, about 95%.

One skilled in the art will recognize that the separation steps can be conducted in any order, for example, fine separation 414 can be conducted before rough separation 410. Preferably, the steps are conducted in the order depicted in FIG. 4.

The liquid mixture remaining at the filter now has a greater concentration of macromolecule 104, and a reduced concentration of soluble fine components 213, e.g., salts. In step 420, the liquid mixture can optionally be combined with additional buffer 422 to adjust the concentration of macromolecule 104 and other components, e.g., ions. Buffer 422 can contain pH buffer, other ionic buffers, filtration aids, denaturation agents, organic solvents, pure water, and the like.

One skilled in the art will recognize that in step 420, buffer 422 can be added to either side of filter 418. Preferably, buffer 422 can be directed through fine filter 416 by applying pressure differential across filter 416. This can dislodge portions of macromolecule 104 that can become attached to fine filter 416 in fine filtration step 414. Also, one skilled in the art will appreciate that steps 414 and 420 can be repeated, providing greater separation of macromolecule 104 from fine components 213.

The concentration of the salt components is preferably reduced in steps 414 and/or 420 by at least 50%, or more preferably, by at least 75%, or most preferably, by at least 90%.

The concentration of the macromolecule is preferably increased by steps 410 and/or 414 by at least 50%, or more preferably, by at least 100%, or most preferably, by at least 200%.

Optional denaturation step 218 accepts the liquid mixture and at least partially denatures macromolecule 104 to prepared macromolecule 104'. The denaturation step can employ denaturing agent 220 and/or a heating step. The denaturing step 218 heats the macromolecule with denaturation agent 220 to, for example, from about 70° C. to about 100° C. for about 60 to about 600 seconds; more preferably, from about 80° C. to about 100° C. for about 120 to about 450 seconds; or even more preferably, from about 85° C. to about 95° C. for about 250 to about 350 seconds. Preferably, denaturation step 218 heats the macromolecule and the denaturation agent to about 90° C. for about 300 seconds.

Figure 5:
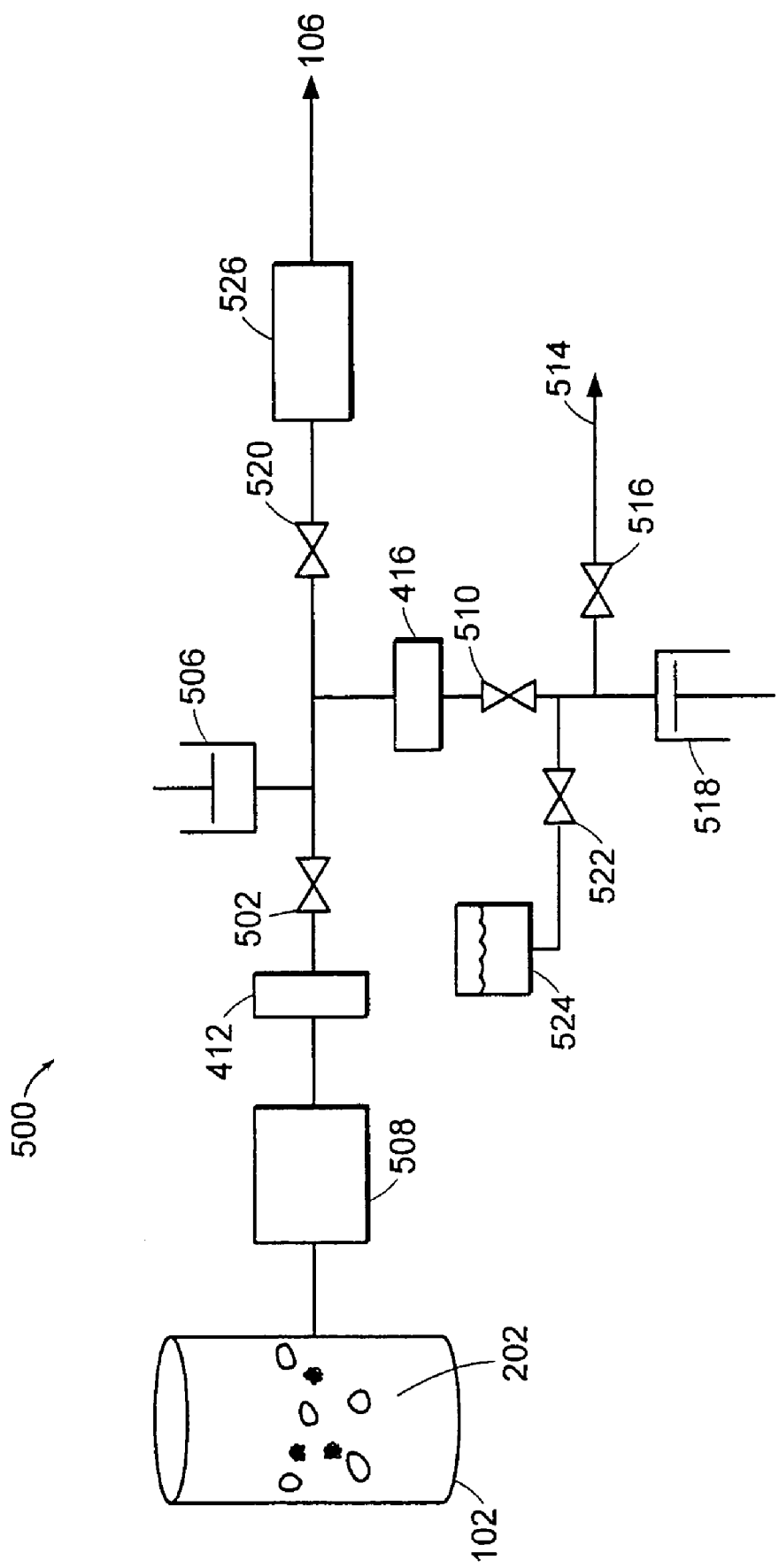
FIG. 5 depicts an apparatus 500 that can conduct the steps in FIG. 4.

FIG. 5 depicts an apparatus 500 that can conduct the steps in FIG. 4. Sampling valve 502 opens to reactor site 102 through rough filter 412. Pump 506 draws the sample through optional lysis unit 508, where lysis step 204 can be performed, and then through rough filter 412, removing rough components from the liquid mixture, i.e., step 410. Valve 502 closes to filter 412 and valves 510 and 516 open, allowing pump 506 to reverse direction and drive the liquid mixture against fine filter 416, passing fine components through fine filter 416 and valve 516 to waste 514, i.e., step 414.

Valve 516 can be closed and pumps 506 and 518 can be operated cooperatively, i.e., pump 506 pushing and pump 518 pulling, to direct a portion of the liquid containing fine components 213 through fine filter 416. When a portion of the liquid mixture has traversed filter 416, valve 510 closes and valve 516 opens, and pump 518 reverses to direct that portion to waste site 514, after which valve 516 closes. As alternatives, only one of pumps 506 and 518 can be employed to direct a portion of the liquid containing fine components 213 through fine filter 416.

To perform step 420, valve 520 can open and pump 506 can direct the remaining liquid mixture containing macromolecule 104 to denaturation vessel 526. Preferably, however, valve 522 opens and pump 518 draws a portion of buffer from reservoir 524. Valve 522 closes, valve 510 opens, and pump 518 directs the buffer through filter 416. Preferably, pumps 518 and 506 operate cooperatively to direct the buffer through filter 416, and pump 506 then directs the mixture through valve 520. Addition of the buffer through the filter can dislodge portions of macromolecule 104 that may become associated with fine filter 416 in step 414.

Next, pump 506 drives the combination of macromolecule 104 to optional denaturation vessel 526, i.e., performing step 218, whereupon the denatured macromolecule 104' can be then directed to analysis site 106.

One skilled in the art will recognize that variations are possible in apparatus 500. For example, one or more of the valves, depicted as two-way valves, could be combined into a single multifunction valve. The placement of various elements can be varied; for example, valve 502 can be placed before rough filter 412, and the like.

Figure 6:
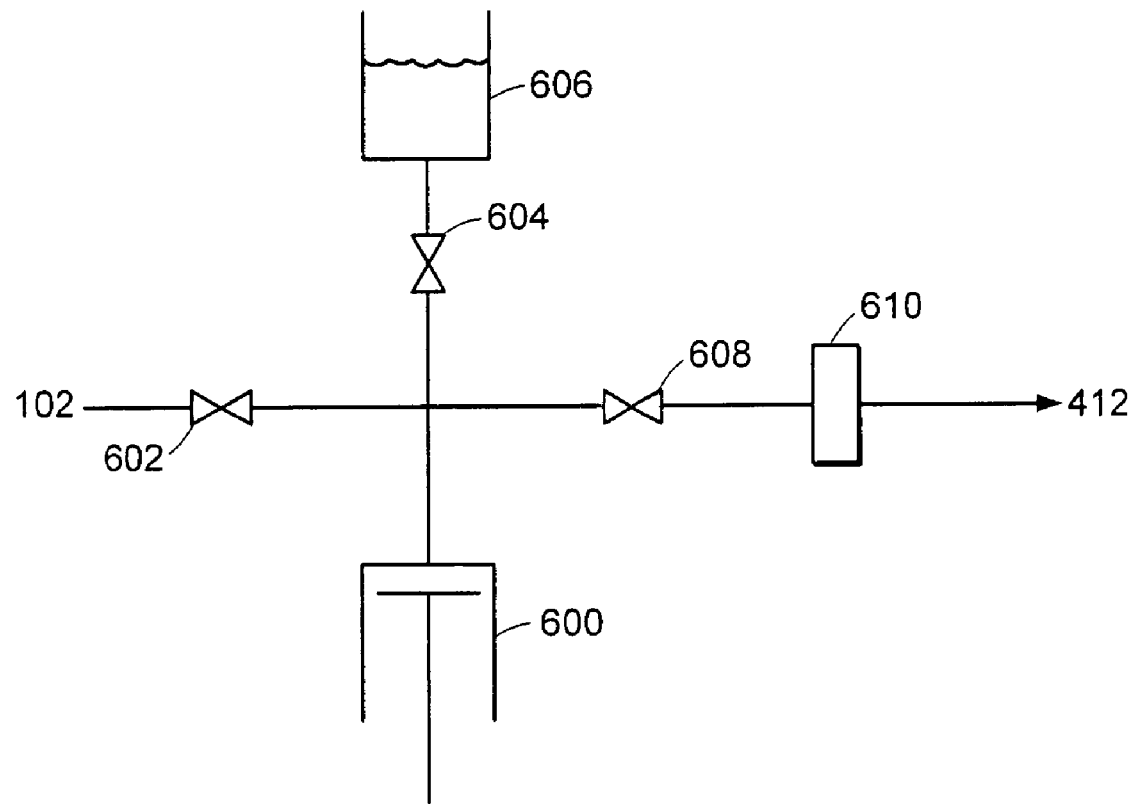
FIG. 6 depicts the lysis module 508.

FIG. 6 depicts lysis module 508. Pump 600 operates to draw liquid mixture 202, including cells, from reactor 102 through valve 602. Valve 602 closes, valve 604 opens, and pump 600 draws a lysis buffer from reservoir 606, lysing at least a portion of the cells in mixture 202. Pump 600 then directs lysed mixture 202' through valve 608 to second stage rough filter 412, preferably through a first stage rough filter 610.

Aseptic Fluidic Interface Coupled to Macromolecule Preparation Apparatus

FIGS. 7A–C, 8, and 9 depict a more detailed schematic of one embodiment of the invention. A controller 701 is coupled to the various pumps, valves, sensors, heating and cooling elements to provide automatic control of the system. The controller may, for example, be a special purpose microprocessor based system or a general purpose computer.

Figure 7A:
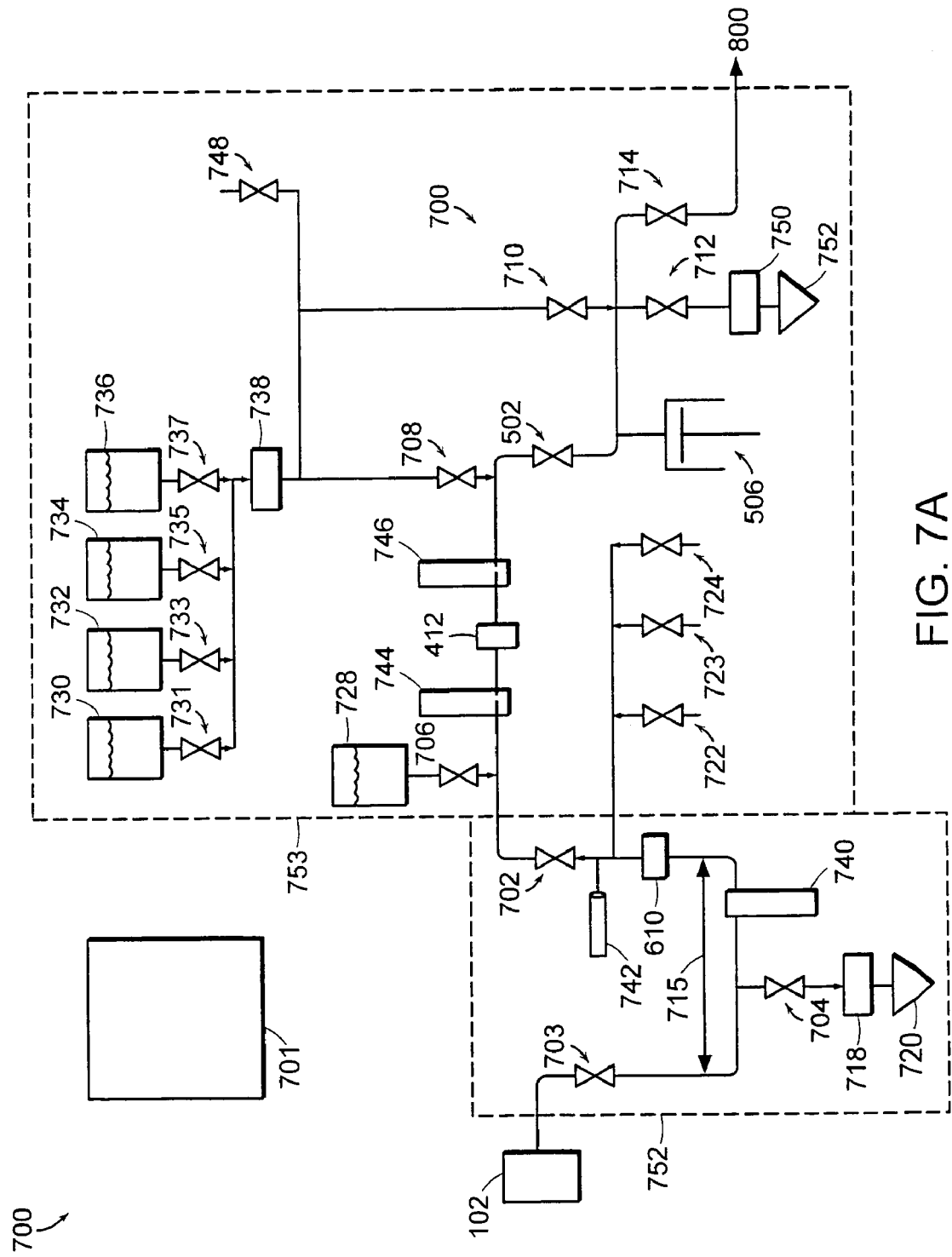
FIG. 7A depicts rough separation circuit 700, containing aseptic separation circuit 752.

FIG. 7A depicts rough separation circuit 700. The liquid mixture can be drawn from bioreactor sample site 102 by opening valves 702, 703, and 502 while closing valves 704, 706, 708, 710, 712, and 714 along the fluid stream. The line from site 102 includes a liquid/air trap region 715, including waste valve 704, waste site 720, and flow sensor 718.

By operating rough pump 506, which is preferably a syringe pump, a sample of liquid mixture 202 can be drawn from reactor site 102 at a flow rate of about 2 mL/min to reach a volume of about 10 mL. This action draws the liquid mixture through initial filtering steps involving first and second stage rough filters 610 and 412. Preferably, first stage rough filter 610 can be selected to remove rough components 60 μm or larger, and second stage rough filter 412 can be selected to remove rough components 5 μm or larger. By closing valve 502, the rough-filtered liquid mixture can be isolated in the syringe chamber of rough pump 506.

Rough separation circuit 700 includes a number of valved reservoirs to supply various standards, buffers and cleaning agents, including size standard reservoir/valve 728/706, cleaning solution reservoir/valve 730/731, run buffer reservoir/valve 732/733, isopropyl alcohol reservoir/valve 734/735, and clean water reservoir/valve 736/737, wherein the amount of buffer drawn can be measured at flow sensor 738. One skilled in the art will recognize that a range of useful solvents and buffers can be employed for cleaning, for standardization, for storage, for aiding filtration, and the like. For example, a size standard buffer can be used in a calibration run of the apparatus to determine the separation performance of the apparatus. The size standard buffer can contain a range of components of known size, at known concentrations, i.e., where size can include weight, molecular weight or diameter of the components. The apparatus can be controlled to self-clean by employing a cleaning solution, preferably cleaning the apparatus between each run of a sample of the liquid mixture. Organic solvents, e.g., isopropyl alcohol, can be employed as cleaning aids or to fill the fluid-handling elements of the apparatus when the apparatus is inactive for an extended period. Clean water and run buffer can be used to dilute the liquid mixture, to adjust the concentration of ions, to aid fluid flow, and the like.

Rough separation circuit 700 also includes a number of pressure transducers 740, 742, 744 and 746, whereby the pressure in the respective portions of the circuit can be measured; compressed air or steam 722, 723, 724, and 748 that can be employed for cleaning or purging the system; flow sensor 750; and waste site 752. The downstream boundary of rough separation circuit 700 is valve 714, through which the liquid mixture can be directed to the desalination/fine filtration circuit 800.

Aseptic Fluidic Interface Apparatus

Figure 7B:
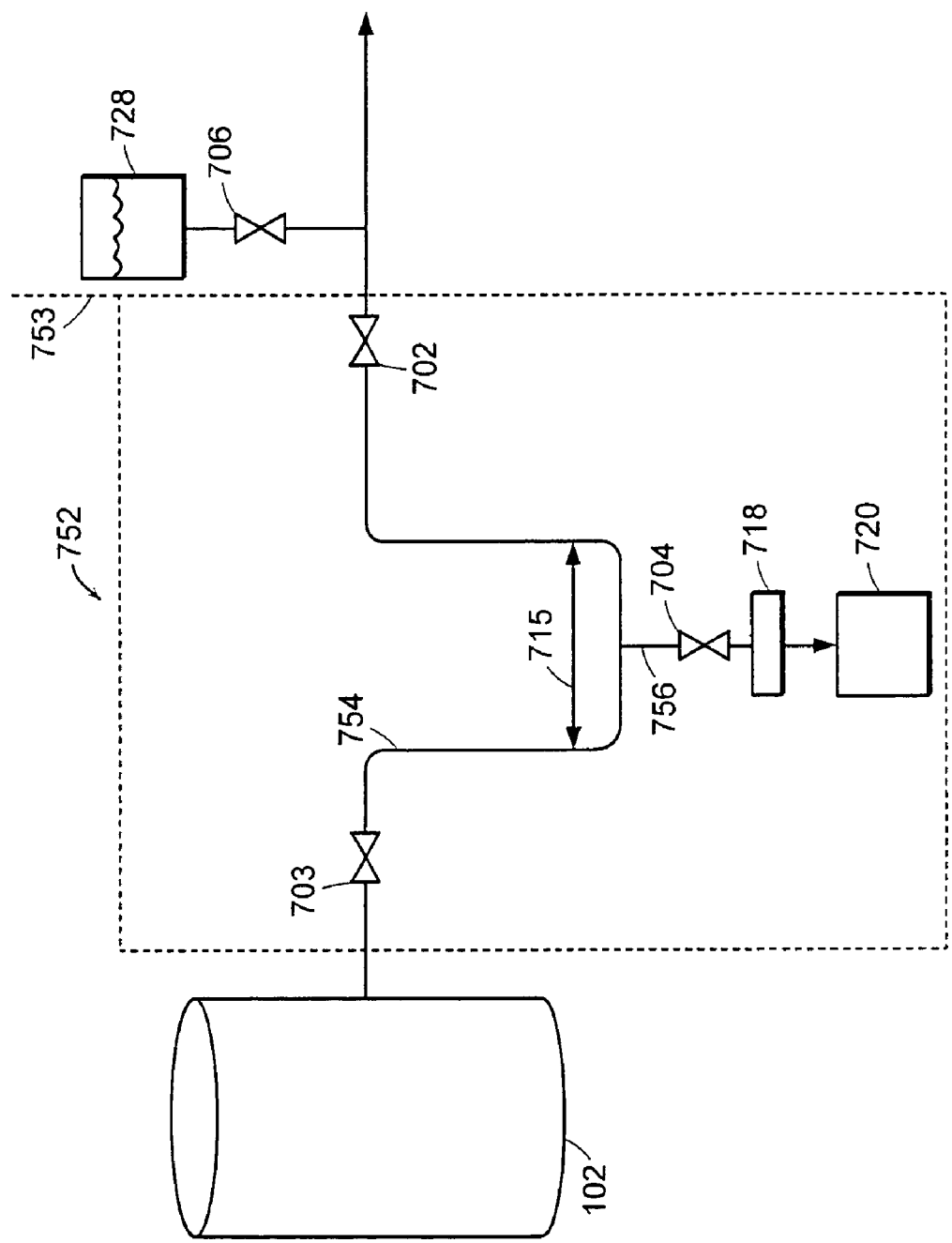
FIG. 7B depicts an aseptic fluidic interface apparatus 752.

FIG. 7B depicts in detail an aseptic fluidic interface apparatus 752 that can be used to provide a fluidic interface between two bioprocess systems, a biofluid source site and a biofluid process site, e.g., bioreactor 102 and apparatus 753 (the balance of rough separation circuit 700).

Inlet valve 703 is coupled to a biofluid source site, e.g., bioreactor 102. A sampling conduit 754 extends from inlet valve 703 to outlet valve 702. Outlet valve 702 is coupled to a biofluid process site, e.g., the apparatus 753. Trap 715 is located at sampling conduit 754. Waste valve 704 is located at a waste conduit 756, and extends from conduit 754 to waste site 720. A wash fluid source is coupled to at least one of the inlet and outlet valves 703 or 702, e.g., as depicted, reservoir/valve 728/706 is coupled through outlet valve 702. The valves are all adapted for automatic control.

Trap 715 is a portion of conduit 754 that is lower in height than either end of the conduit, e.g., so that fluid in the conduit tends to collect there under gravity. The lowest portion of the trap 715 is generally below the lowest end of conduit_754 by a multiple of the conduit internal diameter (or average internal diameter) of at least about 3 times, more typically, at least about 5 times, even more typically about 10 times and preferably at least about 20 times. The trap 715 is typically a U-shaped portion of conduit, and the ends, e.g., at input and output valves 703 and 702 are preferably at the same height. Waste valve 704 can be coupled to any point in the trap 715 but is typically coupled to the lowest point of the trap 715. The volume of the conduits bounded by valves 703, 702, and 704, e.g, the volume of the trap 715, in milliliters, is related to the cross-sectional area of the conduit by a multiplier that is typically less than about 15, more typically less than about 10, even more typically less than about 5, still more typically less than about 2, and preferably less than about 0.5. For example, for a conduit with a cross sectional area of 1 millimeter$^2$, if the factor is 10, the volume is less than about 10 milliliters; if the factor is 2, the volume is less than about 2 milliliters;, and the like.

Aseptic fluidic interface apparatus 752 can control fluid transfer between the two systems so that fluid is transferred in a particular direction at particular times, e.g., only from bioreactor 102 to apparatus 753 during sample collection. For example, automated controller 701 can communicate electronically with the valves, collecting fluid sample from bioreactor 102 by opening inlet valve 703, directing the sample to apparatus 752 by opening outlet valve 702 while waste valve 704 is closed. Reactor 102 and apparatus 753 can be isolated by closing inlet valve 703 and outlet valve 702, and trap 715 and sampling conduit 754 can be drained to waste site 720 by opening waste valve 704. Before transferring a sample, preferably as part of each sample cycle, sampling conduit 754 can be cleaned by opening waste valve 704 and directing a wash fluid through at least one of inlet and outlet valves 703 or 702 and subsequently through the waste valve 704 to waste site 720 e.g., from wash reservoir 728 through outlet valve 702. An optional flow sensor 718 can be located in apparatus 752, typically at sampling conduit 754 or waste conduit 756, preferably at waste conduit 756 between trap 715 and waste site 720. Flow sensor 718 can be employed by controller 701 to sense for fluid flow, particularly when the two biofluid sites, e.g., bioreactor 102 and apparatus 753, are isolated. If flow is sensed during isolation, a possible backflow condition can be indicated. As used herein, "backflow" means undesirable fluid flow in the system, e.g., due to failure of valves 703 or 702 to close, and the like. Backflow can lead to cross-contamination, loss of valuable bioreactor fluid, and the like.

Apparatus 752 preferably controls fluid transfer so the transfer is aseptic. As used herein, aseptic means that the integrity of the sample is maintained. For example, the sample can contain microorganisms, macromolecules, fluids, salts, etc., e.g., those present in bioreactor 102. However, external contaminants, e.g., microorganisms, macromolecules, and other chemical, biological or particulate contaminants from the external environment can be excluded from the apparatus. Furthermore, in the wash process, the residue from each previous sample can be removed from the apparatus. For example, when a process is sampled over time to determine the concentration versus time of a macromolecule, it can be desirable to remove traces of the macromolecule from a previous sample so that the accuracy of a future sample is not affected. Similarly, microorganisms can be removed to avoid a microorganism lodging in the apparatus and excreting amounts of the macromolecule which could affect accurate measurement.

Figure 7C:
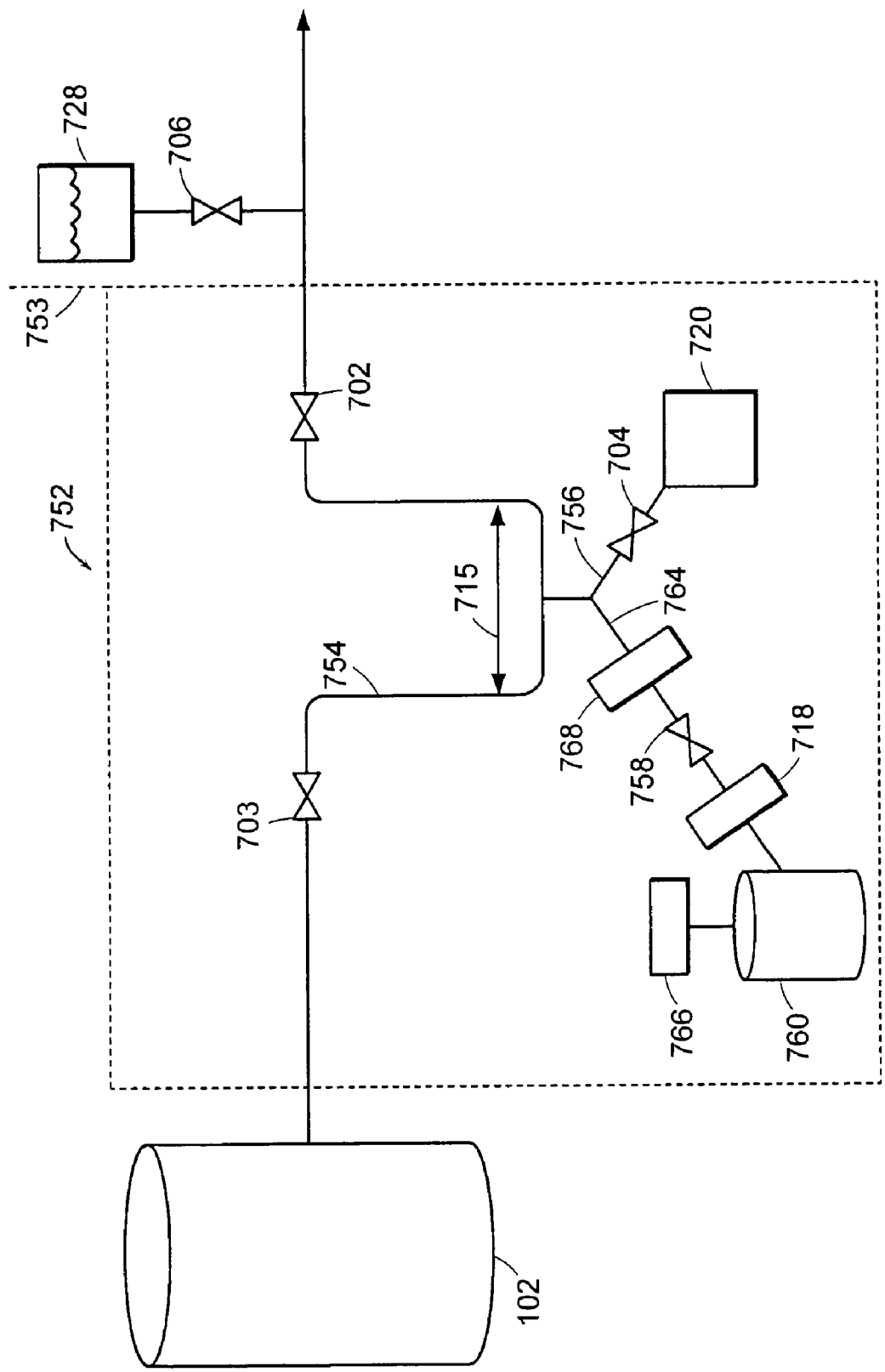
FIG. 7C depicts apparatus 752 with a relief valve 758, overflow reservoir 760, and filter 766.

FIG. 7C depicts an aseptic fluidic interface apparatus 752 with a relief valve 758, overflow reservoir 760, and filter 766, all located on relief conduit 764. Flow sensor 718 can optionally be located on relief conduit 764 as shown. Relief conduit 764 extends from waste conduit 756 at a point between trap 715 and waste valve 704, and ends in fluid communication with the external environment through filter 766. Filter 766 excludes at least a portion of external contaminants from at least a portion of the relief conduit. The filter can be located anywhere between valve 758 and the distal end of conduit 764, preferably at the end as depicted in FIG. 7C. Typically, the filter is selected to exclude microorganisms and particulate contaminants, e.g., the filter excludes contaminants having a diameter greater than about 1 µm, more typically greater than about 0.5 µm, and preferably greater than about 0.2 µm. Overflow reservoir 760 can be located anywhere between valve 758 and the distal end of conduit 764, preferably between the filter 718 and valve 758 as depicted in FIG. 7C. Flow sensor 718, which can be located anywhere in apparatus 752, is typically at waste conduit 756 or relief conduit 764. If the overflow elements are employed, flow sensor 718 is typically at conduit 764 as shown, preferably between valve 758 and reservoir 760. A second filter 768 can be employed at conduit 764, e.g., between valve 758 and trap 715. Filter 768 is sized smaller than filter 766, i.e., excludes at least a portion of contaminants that pass through filter 766. For example, filter 768 is typically sized to exclude particles less than about 75% of the size excluded by filter 766, more typically, less than about 50% of the size excluded by filter 766, an preferably, less than about 25% of the size excluded by filter 766.

Automated controller 701 directs wash fluid into the sampling conduit through at least one of inlet and outlet valves 703 or 702, preferably outlet valve 702. A wash fluid can be one or more fluids, e.g. a gas, a vapor, a liquid, a supercritical fluid, a combination, and the like. For example, gases can include compressed air, oxygen, nitrogen, noble gases nitrous oxide, ethylene oxide, carbon dioxide, and the like; vapor can include steam or vaporized solvents; liquids can include water, aqueous solutions of buffers, antiseptics, detergents, and the like; solvents, e.g., organic solvents such as alcohols, ethers, ketones, polar aprotic solvents, and the like; and supercritical fluids can include carbon dioxide, water, and the like. Typically, the wash fluid is sterile. More than one fluid can be employed, for example, the apparatus can be flushed with an aqueous cleaning solution, steam, and then dry compressed air. Preferably, at least one wash fluid is antiseptic or sterilizing, i.e., is able to kill microorganisms.

The automated controller can direct the wash fluid along a number of paths. Starting from reservoir 728, the fluid can be directed through outlet valve 702, From there, it can be directed through valve 704 to waste 720, or through valve 758 to overflow reservoir 760, or through inlet valve 703 back into reservoir 102.

Automated controller 701 is typically employed with the wash fluid to reduce bacterial count, macromolecule contamination, and/or other contamination to acceptable levels. An "acceptable level" of contamination is that level of contaminants that do not have a measurable adverse effect on the bioprocess site. For example, macromolecule contamination is typically reduced below the detection level of an analysis circuit coupled to the system. Contamination of any portion of the system can be measured using rinse water, e.g., by filling that portion with rinse water, letting stand at 20° C. for 1 minute, and then analyzing the rinse water for the concentration of macromolecules or bacteria. Typically, washing can reduce bacterial contamination, e.g., the number of bacterial colony forming units per milliliter of rinse water to less than about 100, more typically, to less than about 50, and preferably, to less than about 10. Generally, washing can reduce macromolecule contamination in rinse water to less than about 10 parts per million (ppm), more typically, to less than about 1 ppm, even more typically, less than about 0.1 ppm, and preferably, to less than about 0.01 ppm.

Figure 7D:
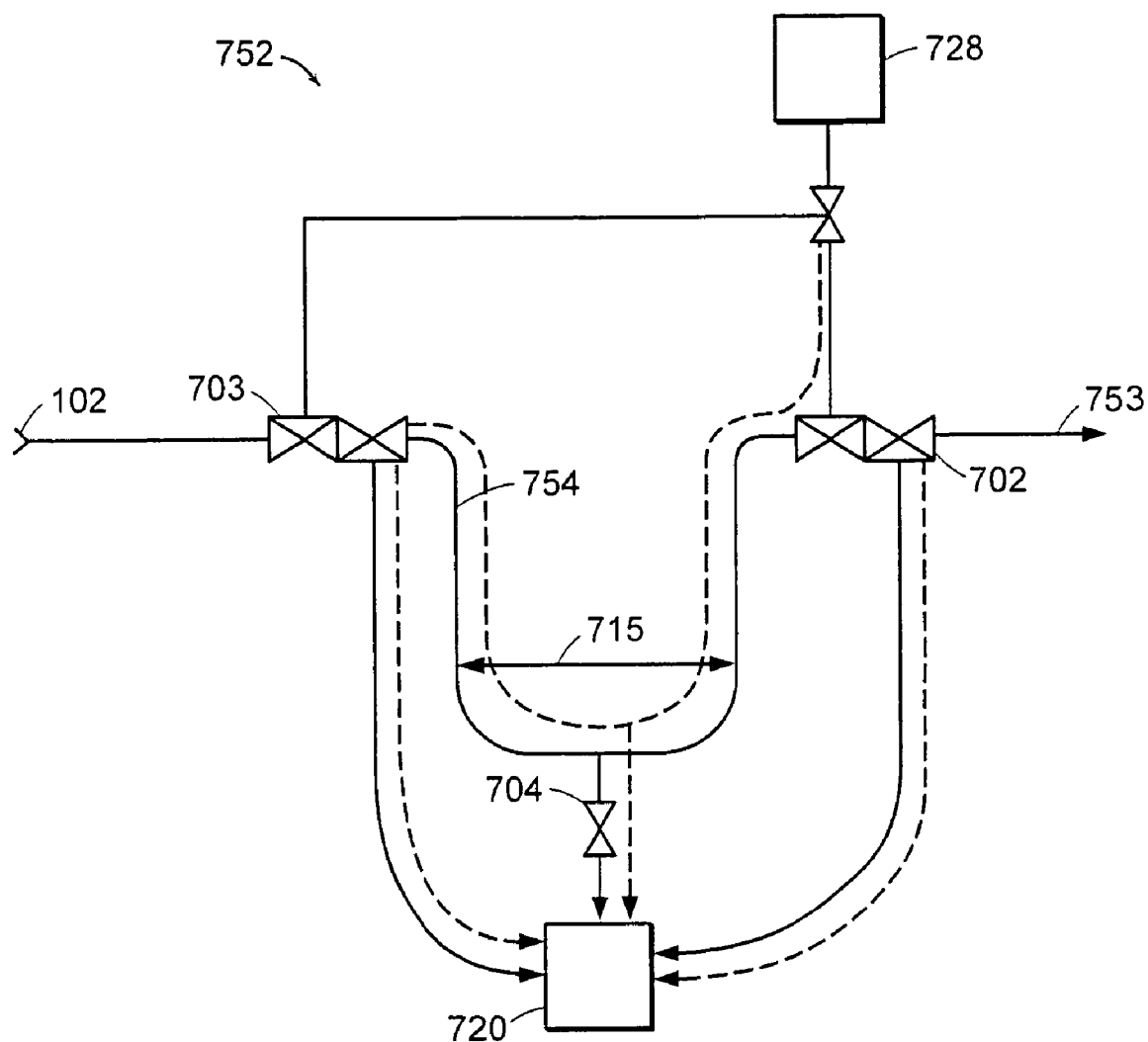
FIG. 7D depicts apparatus 752 wherein inlet and outlet valves 703 and 702 can be double isolated gate valves.

FIG. 7D depicts still other options for apparatus 752. One or more valves, e.g., inlet and outlet valves 703 and 702 can be double isolated gate valves. As used herein, a double isolated gate valve is a single valve unit that can be considered as two coupled three-way valves. Typically, a double isolated gate valve has minimal dead volume between each of its three-way valves. These valves can allow other options for fluid flow. For example, wash fluid can be directed into the system through one such valve, e.g., into outlet valve 703. The wash fluid can then be directed out of the remaining output of double isolated outlet gate valve 703 to waste site 720, or alternatively, into sampling conduit 754, up to double isolated inlet gate valve 702, and then to waste site 720.

Figure 8:
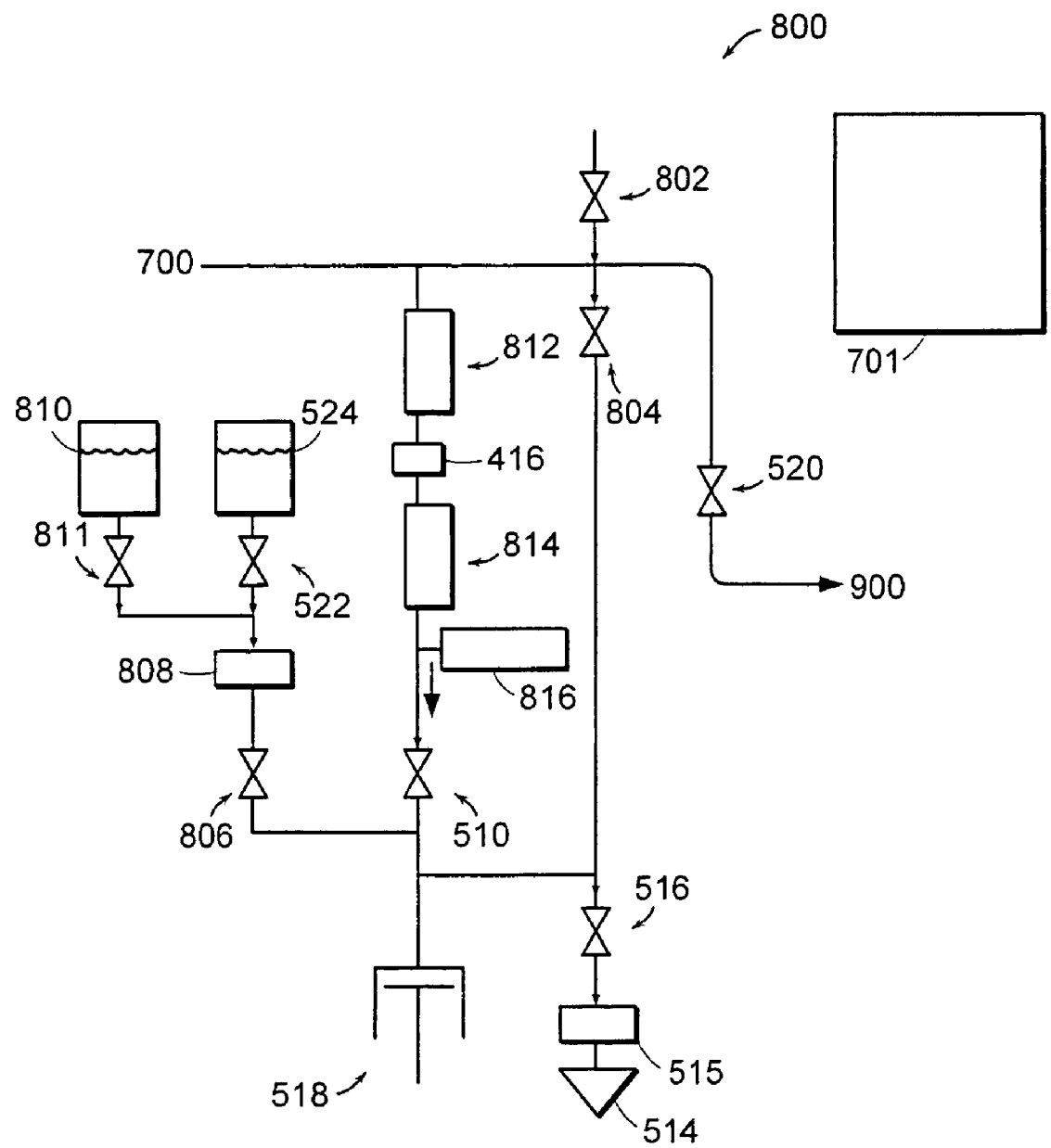
FIG. 8 depicts desalination/fine filtration circuit 800.

FIG. 8 depicts desalination/fine filtration circuit 800, which follows rough separation circuit 700 from FIG. 7A. The liquid mixture, now separated from at least a portion of rough components, can be accepted from rough separation circuit 700. Valves 714 and 510 are opened and branch valves 710, 712, 802, 804, 516, and 520 are closed. Rough pump 506 can be emptied at about 1.5 mL/min to a total of about 7.5 mL. At the same time, fine pump 518 can be controlled to draw the plunger back at about 1.5 mL/min. This creates the force to direct the liquid mixture out of rough pump 506, across fine filter 416 and into the syringe chamber of fine pump 518. Fine filter 416 and rough pump 506 retain the macromolecule while passing a solution of fine, e.g., salt components through and into the syringe chamber of fine pump 518.

Next, valves 510 and 714 are closed, and valve 516 can be opened. Fine pump 518 can be activated to push the syringe plunger contents (about 7.5 mL) at about 1.5 mL/min and direct at least a portion of the liquid mixture containing fine components, e.g., sodium chloride, to waste site 514. Flow sensor 515 can be employed to monitor the liquid sent to waste.

Next, a desalination buffer can be loaded by opening sample buffer feed valve 522, and manifold feed valve 806 and drawing sample buffer from reservoir 524 into fine pump 518. About 7.5 mL of sample buffer can be drawn from reservoir 524, after which sample buffer feed valve 522 and manifold valve 806 are closed. The amount of buffer drawn can be measured at flow sensor 808. Other buffers can be provided, for example, valved reservoir 810/811 can provide, e.g., a pH buffer, pure water, etc.

As described in FIG. 5, to perform step 420, valve 520 can open and pump 506 can direct the remaining liquid mixture containing macromolecule 104 to denaturation vessel 526.

Figure 9:
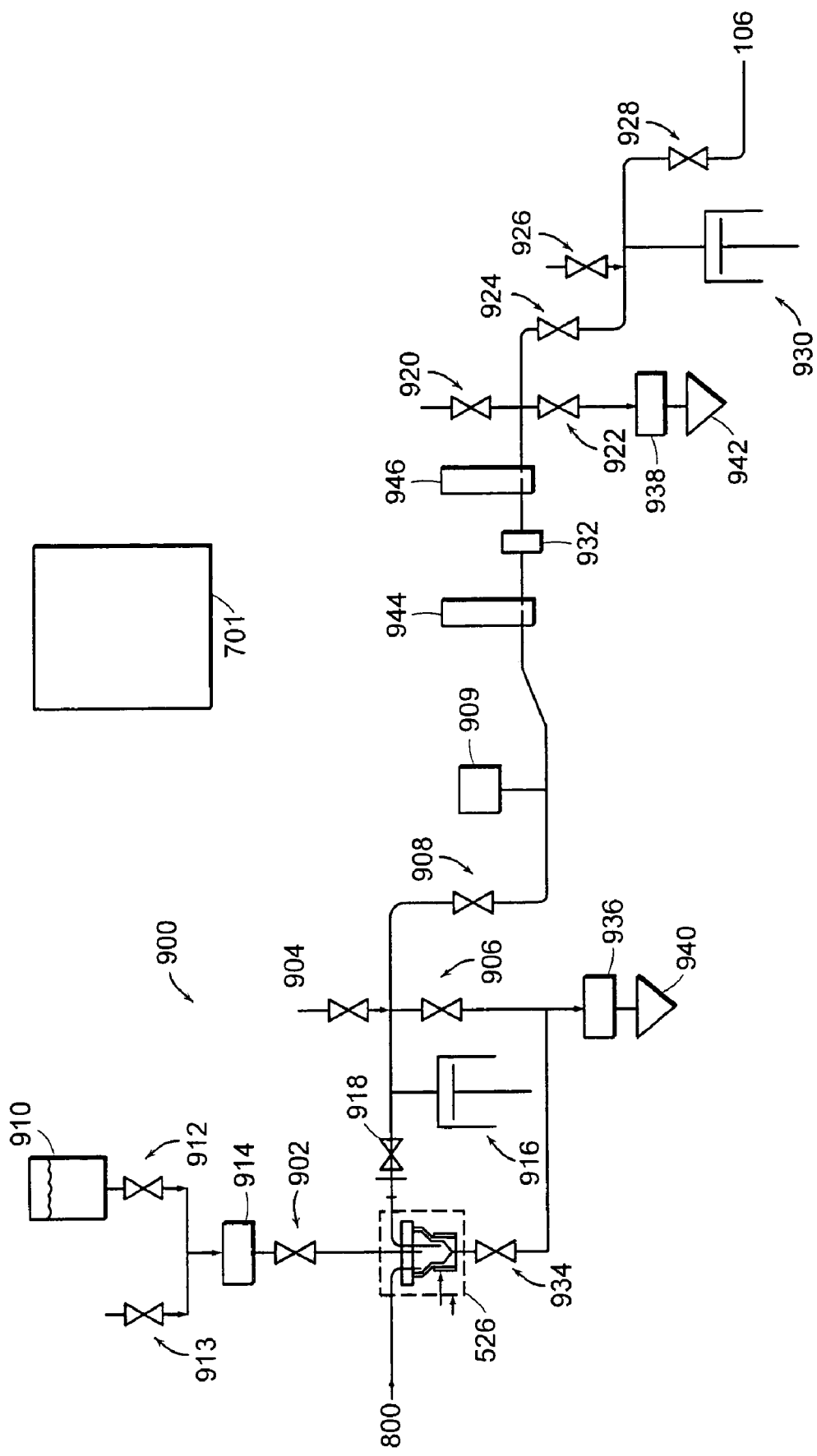
FIG. 9 depicts denaturation circuit 900.
Figure 10:
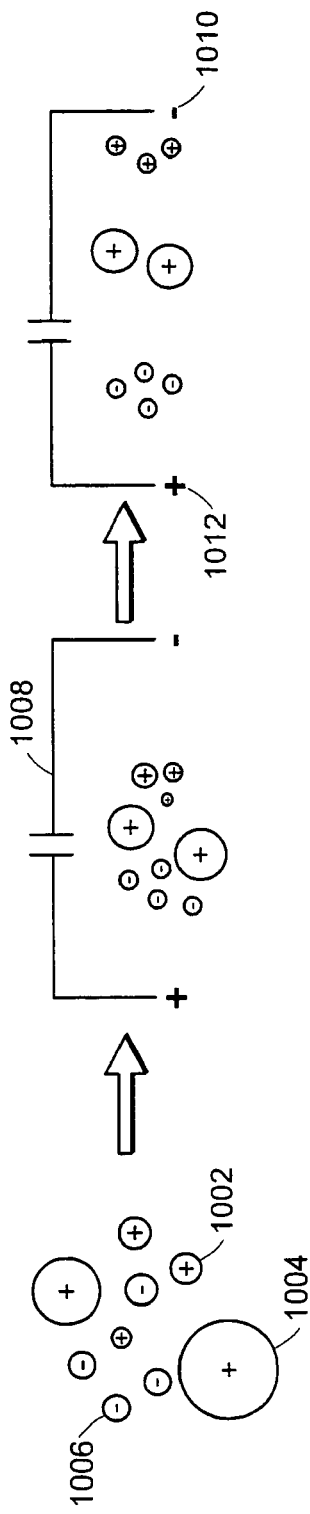
FIG. 10 depicts the separation of a small molecule 1002 and a large molecule 1004.
Figure 11:
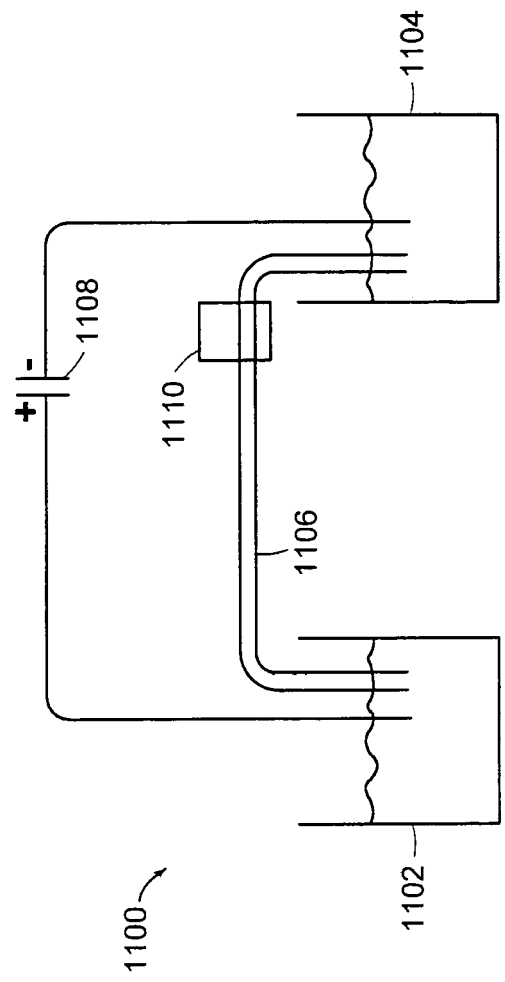
FIG. 11 depicts a schematic of an electrophoresis apparatus 1100.

Next, valves 522 and 806 close, valves 510 and 520 open, and pumps 518 and 506 work together to direct the mixture to denaturation circuit 900, where valves 902, 904, 906, and 908 are closed (see FIG. 9). Pumps 518 and 506 operate at a rate of about 1.5 mL/min. Typically, rough pump 506 will push a total of about 2.5 mL, while fine pump 518 will push a total of about 7.5 mL.

Fine separation circuit 800 also includes a number of pressure transducers 812, 814, and 816, whereby the pressure in the respective portions of the circuit can be measured. Valve 802 can provide compressed air or steam for cleaning or purging the system.

FIG. 9 depicts denaturation circuit 900. Denaturation vessel 526 is preferably a 10 mL stainless steel vessel that contains both heating and cooling coils. The mixture can be heated until at least partial denaturation occurs, for example, heating to at least about 70° C. for about 90 seconds, or more preferably, heating to about 90° C. for about 300 seconds. Subsequently, the cooling coil can be operated to cool the sample to about 25° C.

Upon denaturation, denatured macromolecule 104' can be removed by activating denaturation pump 916, opening valve 902 and opening either valve 912 or 913 to allow the liquid mixture to be drawn from denaturing vessel 526. The concentration of ions in the mixture, for example, the concentration of hydrogen ions, i.e., the pH of the mixture can be monitored at sensor 909. Subsequently, the mixture containing denatured macromolecule 104' can be passed through a precipitate filter 932 by closing valves 918, 920, 922, 926, and 928, and opening valves 908 and 924. Pumps 916 and 930 operate cooperatively, i.e., pump 916 pushing and pump 930 pulling, to drive the liquid mixture against precipitate filter 932. Precipitate filter 932 can be selected to exclude insoluble components that can precipitate during the denaturation step. Preferably, filter 932 excludes insoluble components greater in diameter than about 1 μm, more preferably about 0.6 μm, and most preferably about 0.45 μm. Once the mixture is filtered of at least a portion of precipitate and is in the syringe chamber of pump 930, valve 924 can be closed and analysis site feed valve 928 can be opened, and pump 930 can direct the mixture containing prepared macromolecule 104' to analysis site 106.

Denaturation circuit 900 also includes denaturation vessel valve 934; compressed air or steam inlet valves 904, 920, and 926; flow sensors 936 and 938; waste sites 940 and 942; and pressure transducers 944 and 946.

Stationary Capillary Electrophoresis

Figure 12:
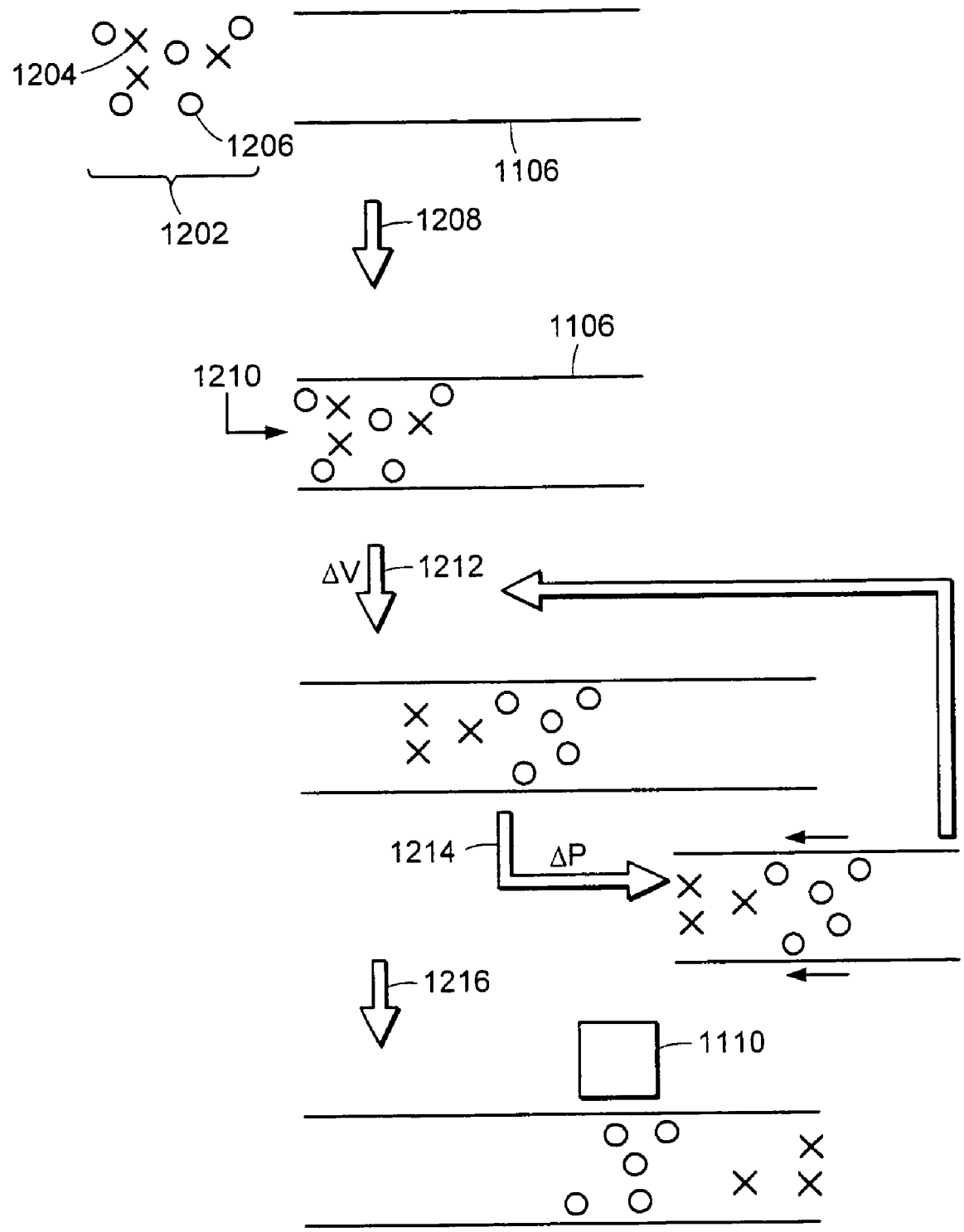
FIG. 12 depicts steps that can be included in analysis by stationary capillary electrophoresis.

FIG. 12 depicts steps that can be included in analysis by stationary capillary electrophoresis. A liquid sample 1202 includes one or more molecular analytes 1204 and other components 1206. As used herein, a molecular analyte is any molecule that is soluble or suspended in the liquid sample and has an electrophoretic mobility that is different from other components 1206 in the liquid sample. The molecular analyte can be any molecule, e.g., inorganics, small molecule organics, biomolecules, synthetic polymers, biopolymers, proteins, peptides, amino acids, nucleic acids, and the like. Preferably, the molecular analyte is a macromolecule, i.e., macromolecule 104, and most preferably, separated macromolecule 104'.

The liquid sample is introduced to the end of an electrophoresis column 1106 by pressure or electro-kinetic injection in step 1208. A buffer 1210 that contains, for example, electrolytes know to the art to be suitable for capillary electrophoresis can be added. Additional components of the buffer known to the art can include organic solvents, e.g., acetonitrile; additives which can act to reduce electroosmotic flow; electrophoretic flow modifiers, i.e., ionic agents that complex with molecular analytes to change electrophoretic mobility; spectroscopic or radioactive tags; and the like.

A voltage differential is applied across the column in step 1212, causing the molecular analyte to separate from other components. In optional step 1214, pressure differential can be applied to the column to cause liquid in the column to flow. For example, the effective length of the column can be increased, e.g., by conducting a partial electrophoretic separation step 1212, pausing, performing optional step 1214 to flow liquid in the column in a direction contrary to the electrophoretic flow, and then resuming electrophoretic flow step 1212. One skilled in the art will appreciate that steps 1212/1214 can be repeated numerous times. Once the molecular analyte is separated, it can be analyzed in detection step 1216, either while still in the column by detector 1110, as depicted, or after extraction from the column.

Figure 13:
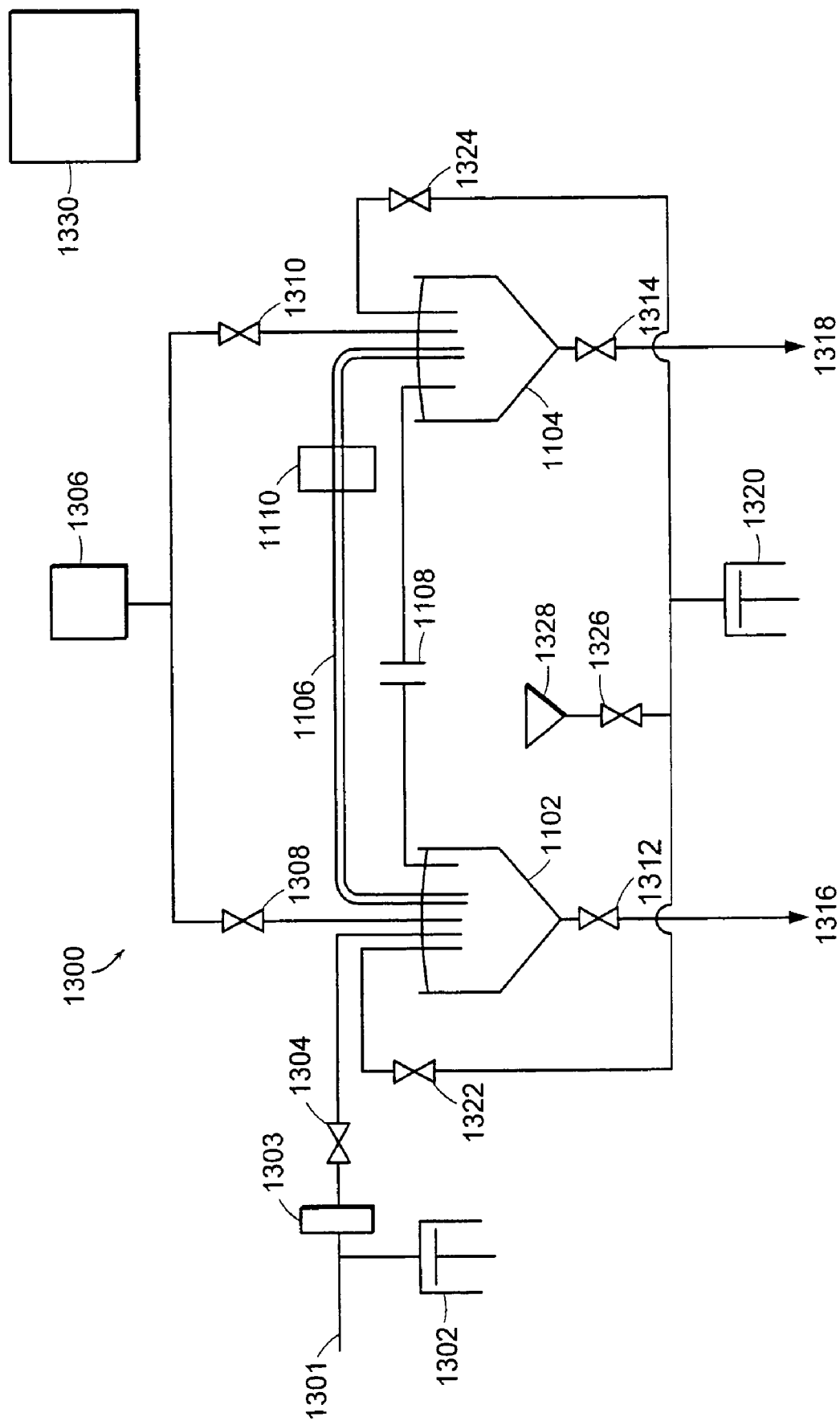
FIG. 13 depicts a stationary capillary electrophoresis circuit 1300 that can be controlled to conduct the steps in FIG. 12.

FIG. 13 depicts a stationary capillary electrophoresis circuit 1300 that can be controlled to conduct the steps in FIG. 12. The inlet chamber 1102 is supplied with the liquid sample by pump 1302 through inlet valve 1304 from liquid sample source 1301. Optional precipitate filter 1303 can be employed to separate insoluble precipitates from the liquid sample by employing pump 1302 to apply the liquid sample to filter 1303 with a pressure differential across the filter.

Each chamber can be supplied independently by a buffer reservoir 1306 through valves 1308 and 1310. Each chamber can be independently drained via valves 1312 and 1304 to waste sites 1316 and 1318. Pump 1320 can draw filtered air through air inlet valve 1326 and air source 1328, and independently direct the air to chambers 1102 and 1104 through valves 1322 and 1324. The valves, pumps, optional electrophoresis power supply 1108, and optional detector 1110 are adapted to be controlled by an optional controller 1330.

The capillary electrophoresis column 1106 is coupled with the interior of each chamber so that liquid in each chamber can be placed in fluid communication with the respective end of column 1106. Preferably, the column has a length of at least about 20 centimeters, more preferably at least about 30 centimeters, and most preferably, at least about 50 centimeters.

The optional detector 1110 can be any detection method known to the art for detection of molecular analytes, for example, absorbance/transmission of radiation, e.g. ultraviolet/visible light; fluorescence detection; refractive index detection; electrochemical detection; mass spectrometric detection; detection of electron or nuclear magnetic resonance; flame ionization detection; binding, e.g., in an enzyme or antibody assay; detection of a spectroscopic or radioactive label; and the like. When optional detector 1110 is an optical detector, it can be configured to detect molecular analytes that are inside column 1106. Or, fractions can be collected from the molecular analytes exiting column 1106, e.g., at outlet chamber 1104, and the fractions can be analyzed separately from the column.

Additionally, each chamber can be barometrically sealed, i.e., they can be pressurized or depressurized. For example, valves 1304, 1308, 1312, 1324, and 1326 can be closed, valve 1322 can be opened, and pump 1320 can pressurize inlet chamber 1102. If the pressure in chamber 1102 is greater than the pressure in outlet chamber 1104, a high to low pressure differential results across the length of capillary electrophoresis column 1106. Alternatively, pump 1320 can reduce the pressure in chamber 1102 to less than the pressure in chamber 1104, resulting in a low to high pressure differential, which can direct liquid from chamber 1102 through column 1106 to chamber 1104. Or, the valves can be configured so that pump 1320 can pressurize or depressurize chamber 1104. Optionally, separate independent pumps can be coupled with each chamber and the pumps can operate cooperatively, one pulling and the other pushing, to create a pressure differential across column 1106. Creation of a pressure differential between chamber 1102 to chamber 1104 through column 1106 can be employed to fill, purge, or clean the column, or to move fluid through the column, e.g., perform step 1214.

Figure 14:
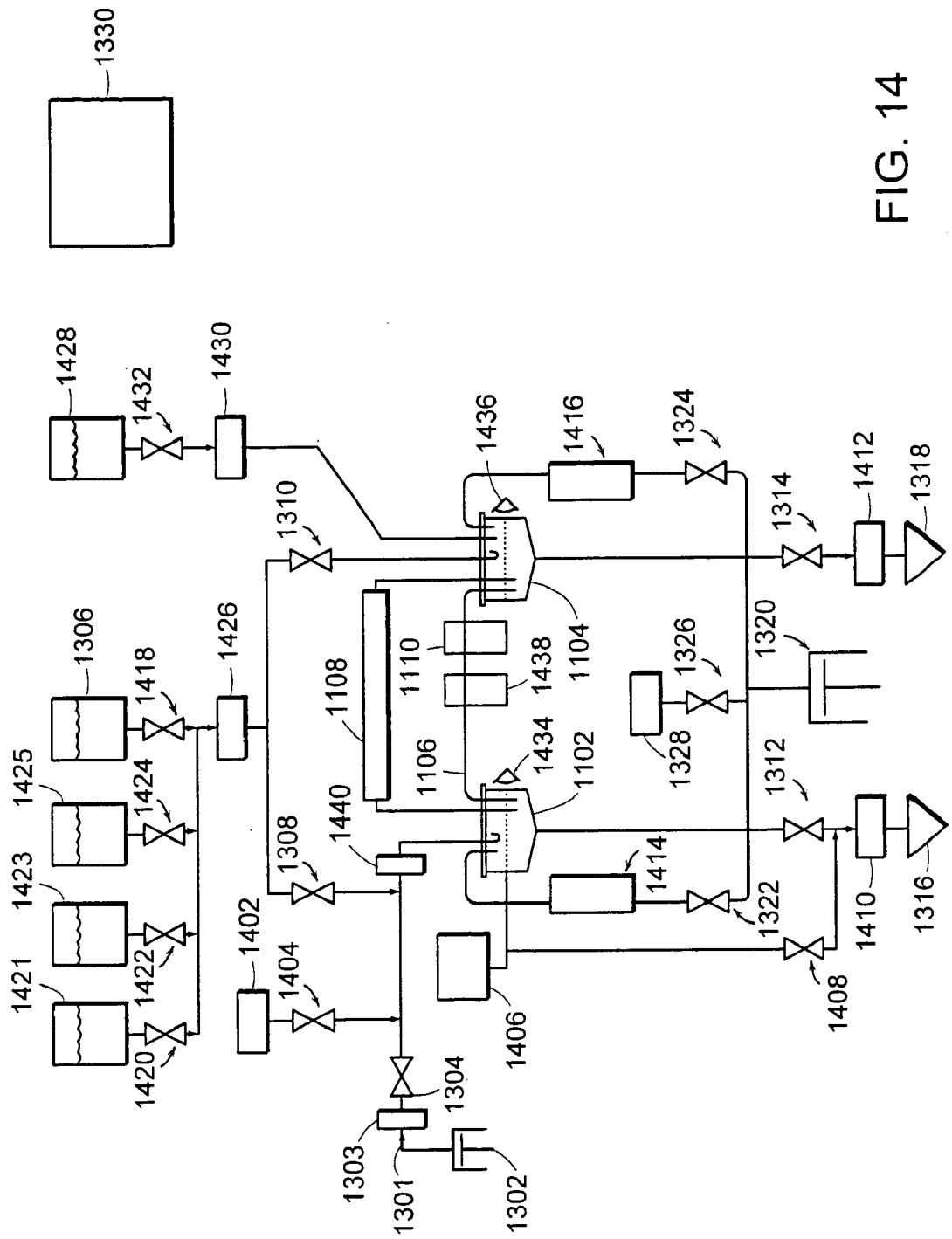
FIG. 14 depicts a more detailed schematic of the capillary electrophoresis circuit.

FIG. 14 depicts a more detailed schematic of the capillary electrophoresis circuit. The line between inlet valve 1304 and inlet chamber 1102 can be supplied with compressed air by filtered air supply 1402 through valve 1404. An additional optional air source 1406 and valve 1408 is provided that can be employed to purge inlet chamber 1102 and/or the waste line between valve 1312 and waste 1316. The waste from both chambers is provided with flow sensors 1410 and 1412, respectively. Pressure transducers 1414 and 1416 are provided to sense the pressure in the apparatus. Along with reservoir 1306 are provided a valve 1418 and additional valved reservoirs 1420/1421, 1422/1423, and 1424/1425. These reservoirs can supply water, buffer, cleaning solution, solvents, electrolytes, and the like, the flow of which can be sensed at flow sensor 1426. Additional buffer can be supplied to the outlet chamber 1104 by reservoir 1428 through flow sensor 1430 and valve 1432.

Additionally, the level of fluid in chambers 1102 and 1104 can be sensed independently by level sensors 1434 and 1436, respectively. Heat generated in column 1106 by the electrophoresis current can be removed by a heat exchanger 1438, which can be, for example, a cooling element, a thermoelectric element, and the like. Also, optional degas unit 1440 can be employed to remove at least a portion of dissolved gases.

Figure 15:
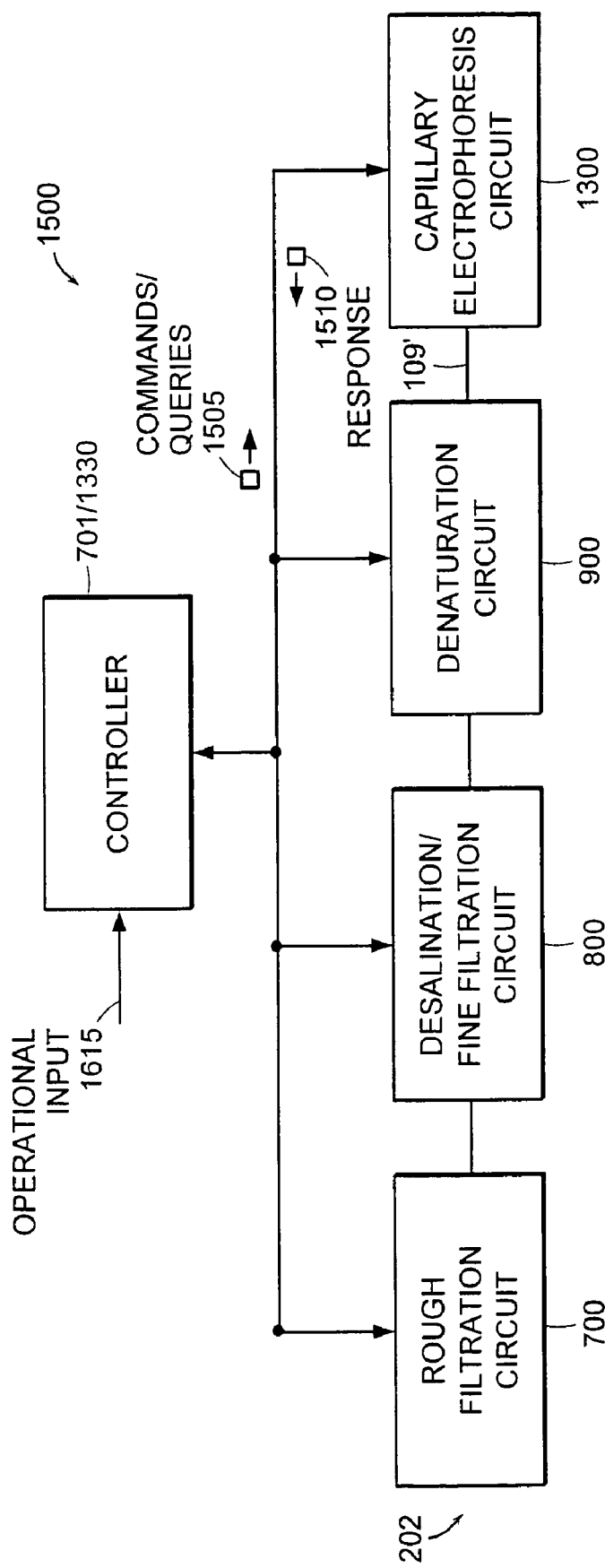
FIG. 15 depicts a block diagram of a preferred apparatus 1500.

Automated System for On-Line Aseptic Sampling of Bioreactor Fluids, Macromolecule Separation, Denaturation, and Capillary Electrophoretic Analysis FIG. 15 depicts a block diagram of a preferred apparatus 1500, which couples rough filtration circuit 700, desalination/fine filtration circuit 800, denaturation circuit 900, and capillary electrophoresis circuit 1300 into an integrated system. That is, rough filtration circuit 700 inputs a complex liquid mixture 202 comprising a macromolecule, and separates the macromolecule from rough components. The mixture is directed to desalination/fine filtration circuit 800, and the macromolecule is separated from at least a portion of fine components, including salt components. The mixture is then directed to denaturation circuit 900, where the macromolecule is denatured and separated from any insoluble precipitates that form during denaturation. This creates a liquid sample, containing denatured macromolecule 104', that can be directed to capillary electrophoresis circuit 1300. In this view, several elements described in preceding Figs. can be synonymous, e.g., pumps 930 and 1302 can be the same pump; valves 928 and 1304 can be the same valve; filters 932 and 1303 can be the same filter; and automated controllers 701 and 1330 can be the same controller.

One skilled in the art will appreciate that the various elements of apparatus 1500 can be integrated in different combinations. For example, each of the various individual elements can be integrated with a bioreactor, for example, rough filtration circuit 700 can be integrated with a bioreactor, or denaturation circuit 900 can be integrated with a bioreactor, and the like. Combinations of the various elements van also be employed, for example, for a particular biofluid source that does not require rough filtration or denaturation, aseptic interface 752 can be combined with fine filtration circuit 800 and capillary electrophoresis circuit 1300. In another example, a system that does not require fine filtration could employ rough separation circuit 700, denaturation circuit 900, and capillary electrophoresis circuit 1300. In other applications, each circuit or apparatus can be used alone, or in other logical combinations. One skilled in the art will know which circuit or apparatus will be useful in any particular application.

In various embodiments, each of the individual elements in apparatus 1500 and various combinations thereof can be coupled "on-line" to an operating bioreactor. As used herein, "on-line" means that the apparatus can draw samples directly from the reactor into the apparatus, i.e., the sample is drawn directly into the apparatus without exposure to the external environment and without involving a transfer using a discrete sample container, e.g., a sample vial.

Another feature of particular embodiments of combinations of two or more of the elements of apparatus 1500 is that each combination can be coupled to an operating bioreactor to form an integrated system. This means that the sample is in complete custody of the system, i.e., is controlled to be free from exposure to the external environment, from the bioreactor to the final operation on the sample (e.g., analysis of the prepared macromolecule at capillary electrophoresis circuit 1300). Furthermore, "integrated" can mean that the various circuits and apparatuses are controlled by the automated controller to operate in a coordinated fashion.

Still another feature of various embodiments of the elements of apparatus 1500 and their combinations is that each can be coupled to an operating bioreactor to handle "raw" fluids, i.e., complex liquid mixtures containing one or more components typically found in a bioreactor, for example, cells, cellular debris, cell organs, cell fragments, salts, macromolecules including proteins, DNA, RNA, and the like. A "raw" fluid is taken directly from a reactor, typically an operating reactor, without any preprocessing.

In particular embodiments, the capillary electrophoresis circuit 1300 can be controlled to partially or completely exchange the fluid inside the capillary electrophoresis column in place, i.e., the column can remain fixed with respect to one, or preferably both of the inlet and outlet reservoirs.

In various embodiments, the inside diameter of the capillary electrophoresis column is at least about 50 µm, more typically at least about 75 µm, and even more typically at least about 100 µm. One skilled in the art will know that values larger than 1 mm for the inside diameter of the capillary are possible, but can face diminishing returns in terms of efficiency. In a particular embodiment, the inside diameter of the capillary is from about 50 µm to about 150 µm., or more particularly, from about 100 µm to about 125 µm.

In various embodiments, each system, circuit and apparatus can draw sample volumes from at least about 0.1 mL to at least about 25 mL, and more typically between about 0.5 mL and about 10 mL. In a particular embodiment, the sample volume is between about 0.75 and about 5 mL.

The inside diameter of the conduits employed in the various circuits in the system, excluding the capillary itself, can be in various ranges. The inside diameters can be different in different portions of the system. The inside diameters are typically in a range of from about 0.5 to about 10 millimeters (mm), more typically between about 0.75 and about 5 mm, even more typically between about 0.75 and about 2 mm, and preferably between about 1 and about 2 mm.

The "pressure differential" employed to direct components at or through a filter can be estimated by one skilled in the art by considering relevant system characteristics such as filter pore size, fluid viscosity, approximate concentration of material larger than the filter pore size, time to filter a particular volume, flow rate, and the like. One skilled in the art will know how to use such characteristics to choose an appropriate pressure differential based on the desired filter performance and flow rate. Typically, the pressure differential across the filter is between about 500 and about 7000 millibar, more typically between about 1000 and about 5000 millibar, or even more typically between about 1500 and 3000 millibar. A "pressure differential" can be caused by pressurizing one side of the filter, depressurizing on one side of a filter, or a combination of pressurizing one side and depressurizing the other side in a "push-pull" fashion.

As used herein, the filters are employed as "direct flow" or "dead-end" filters, and filtration methods employed herein are "direct flow" or "dead-end" filtration methods. This means that during filtration, the pressure differential applied causes the liquid mixture being filtered to be applied directly to the filter, i.e., in a direction substantially perpendicular to the face of the filter.

Another particular embodiment of the filters and filtration methods employed is a "back-flushing" capability. That is, each filter can be cleaned by directing a fluid, e.g., a buffer, a cleaning fluid, water, a solvent, a desalination buffer, a denaturation buffer, combinations thereof, and the like through the filter in a direction opposite to a previous filtration step. For example, a filter which becomes clogged with debris after a filtration step can be cleaned, at least in part, by directing a fluid through the filter in a direction opposite to the direction of the preceding filtration step.

The controllers 701/1330 may receive operational input 1615 from an external source, such as a local user interface (not shown). The controller(s) 701/1330 process the operational input 1615 to send commands or queries 1505 to the circuits 700, 800, 900, or 1300 and, in some embodiments, receive responses 1510 from these circuits.

Figure 16:
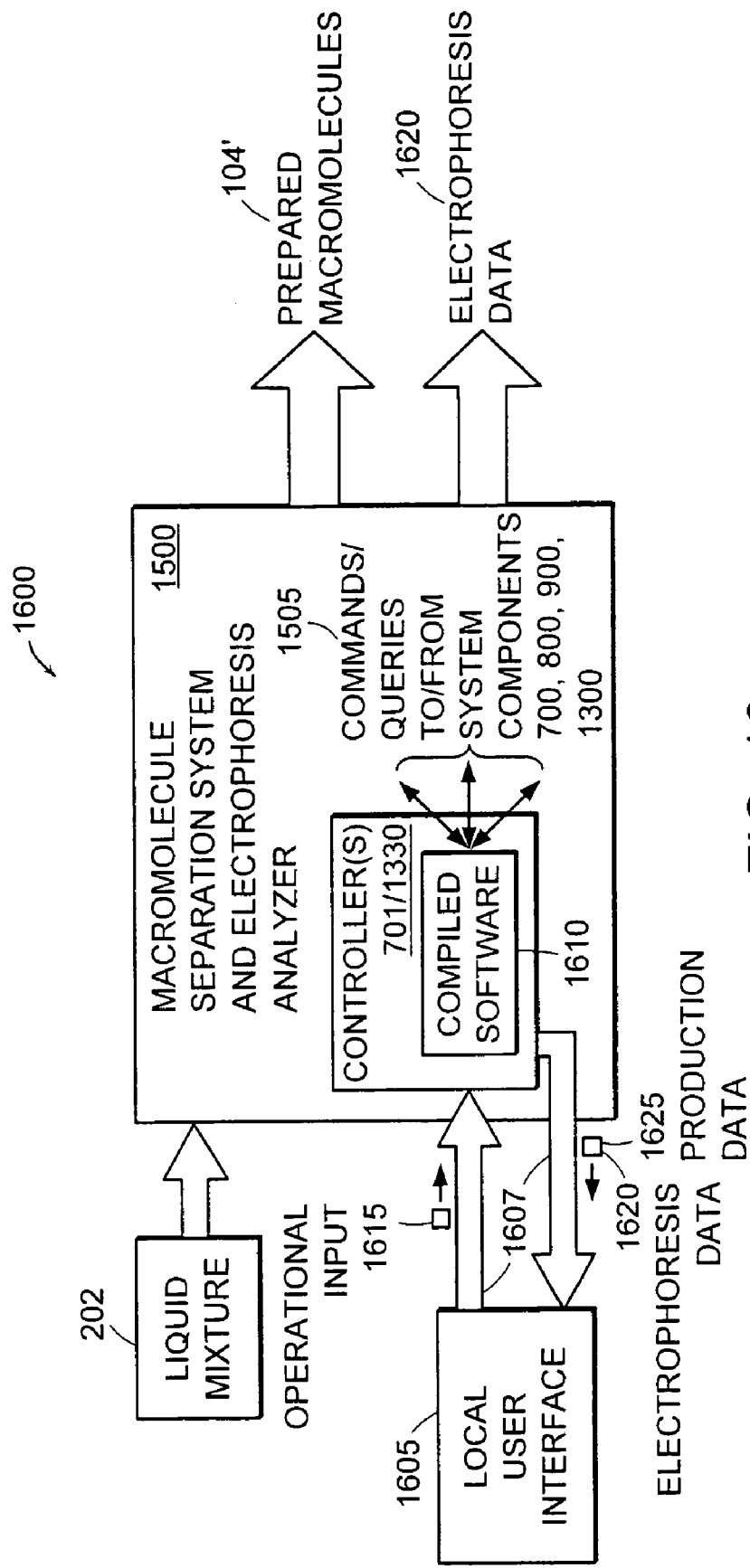
FIG. 16 is a block diagram of a system including the subsystems described above and a local user interface for providing operational input.

FIG. 16 is a block diagram of an overall system 1600 shown in the context of additional external systems and input/output data related to the system 1500.

From a macromolecule processing point of view, this overall system 1600 refers to the system 1500, the liquid mixture 202 that includes a macromolecule of interest, and the prepared macromolecules 104'.

From a controls point of view, the overall system 1600 includes the system 1500, controller(s) 701/1330 in the system 1500, and local user interface 1605 connected to the system 1500 via a bus or local area network 1607.

The controllers 701/1330 may include executable instructions, provided in the form of software or firmware, which is preferably unchangeable by the user of the system 1500. Such unchangeable software may be referred to, and is referred to hereafter, as "compiled" software, meaning that source code was compiled (e.g., compiled C code), and the compiled software exists only in a form usable by the controllers 701/1330. Source code may be provided to the user for re-compiling to facilitate modification of the configuration or general operation of the system. However, re-compiling may cause a re-validation and/or re-approval of the system 1500 to be required before further usage, which is discussed later in reference to FIGS. 18–23.

The operational input 1615 can be provided or written by a designer or end user of the system 1500 without having to recompile the compiled software. The operational input 1615 typically provides specific operational instructions to customize operation of the system, which may be limited by the compiled software according to a predefined set of limits.

The local user interface 1605 may include a general purpose computer or custom-designed computer specific for operating the system 1500. The local user interface 1605 may send the operational input 1615 to the controllers 701/1330, which process the operational input 1615 using the compiled software 1610. Responsively, the compiled software 1600 may send commands or queries 1505 to the system components 700, 800, 900, and 1300 via an internal bus or network (not shown).

The compiled software 1610 may be stored locally or downloaded across the network 1607 and is executed by the controllers 701/1330. The compiled software 1610 may also be permanently stored in the controllers 701/1330 through the use of firmware, Field Programmable Gate Arrays (FPGA's), Read-Only Memory (ROM), and so forth.

The controllers 701/1330 may also collect data, such as the production data 1625 and/or electrophoresis data 1620, during operation of the system 1550. These data 1620, 1625 may be sent via the network 1607 to the local user interface 1605 for further processing or display to the user via a Graphical User Interface (GUI), other display, such as LED indicators, or output as sound, such as produced by an audio synthesizer.

The electrophoresis data 1620 may include information regarding the prepared macromolecules 104'. For example, the electrophoresis data 1620 may include the molecular weight of the sample and time corresponding to how long the sample takes to travel across the length of the electrophoresis column 1106.

The production data 1625 may include information regarding the system 1500, such as calibration information, such as throughput/recovery and molecular weight calibrations, equipment specifications, such as capillary diameter, voltage levels, capillary length, cleaning solutions, and number of usages since the last replacement of the electrophoresis column.

The production data 1625 may also include information related to the production of the macromolecules from the liquid mixture 202, such as discussed in reference to FIG. 5.

The compiled software 1610 may have knowledge of a mapping, in accordance with a known industry standard between the operational input 1615 and system components 700, 800, 900, or 1300, including subcomponents, such as pumps, valves, heating or cooling elements, pressure sensors, etc. The compiled software 1610 is preferably tested and integrated by the manufacturer of the system 1500 in a manner also consistent with known industry standards, such as American National Standards Institute (ANSI) (e.g., ANSI 'C' programming language).

For example, the manufacturer may validate the system by (i) inputting a complete set of test vectors to the controllers 701/1330 in a testing phase of the system 1500 and (ii) observing activation/deactivation of the valves, pumps, etc. in accordance with the test vectors. Prior to release of the compiled software with the system 1500, the compiled software 1610 may be tested extensively for failure modes and/or error checking capabilities for detecting programmatic or out-of-range errors identified in the operational input 1615. Other forms of testing may include providing test vectors with erroneous or harmful information to ensure the compiled software 1610 handles these situations in a manner that protects the system 1500 or components therein.

In a preferred embodiment, when sold or released to a customer, the compiled software 1610 is unchangeable by the customer. In other words, the customer cannot alter the compiled software 1610 and, therefore, the system 1500 continues to operate and be controlled in a manner tested and validated by the manufacturer of the system 1500. The operational input 1615, however, can be modified by the customer independent of the compiled software 1610 to customize the operation of the system. For example, if a particular macromolecule requires additional filtering cycles or denaturation dwell time, the customer may customize the operational input 1615 to provide such control.

The operational input 1615 may be declarative software instructions, where declarative software instructions are defined as instructions of a relational language or functional language, as opposed to an imperative language, where imperative (or procedural) languages specify explicit sequences of steps to follow to produce a result. Declarative languages, in contrast, describe relationships between variables in terms of functions or inference rules, and a language executor (i.e., interpreter or compiler) applies some fixed algorithm to these relations to produce a result.

Thus, for example, the operational input 1615 may be software instructions, such as BASIC software instructions, that are interpreted in a real-time or pseudo-real-time manner by the compiled software 1610. The operational input 1615 may also be forms of data streams that are produced by a graphical user interface (GUI) and processed by the compiled software 1610.

An example set of program instructions or portion of operational input is listed below. The program instructions form a representative script for operating an analyzer, such as the capillary electrophoresis circuit 1300. The representative script may be referred to as a physical layer between the user and the compiled software 1610 to permit a chemist or operator to program the operation in an english-like language that provides an intuitive understanding for the programming. Use of this technique permits the manufacturer of the system 1500 to "hard code" the physical operation of the system 1500 while permitting the end user to "soft code" the operational input 1615 for customizing or modifying a process based on empirical or calculated process flows.

```
"%" Denotes comment and is not executed
% script - flow to Desalting Filter
%
% begin Push Sample to Desalt Filter Routine
echo "Push Sample to Desalt filter."
open_valve SV1022          %   open 'Pump - Desalt Isolation Valve-
                                   SV1022' (FIG. 8, valve 714)
sleep 1.0                  %   Pause 1 second
open_valve SV1026          %   'open - Pump 2 -Desalt Isolation
                                   valve-SV1020'
                                   (FIG. 8, valve 510)
sleep 1.0                  %   Pause 1 second
% watch_pressure_drop         <pt1>, <pt2>, <time_in_seconds>,
                              <warning_low>, <warning_high>,
                              <error_low>, <error_high>
watch_pressure_drop PT4, PT5, 10.0, 0, 10, −5, 20
% move sample across filter(s) by activating syringes
start_syringe SY1, PUSH, 7.5, 0.6
start_syringe SY2, PULL, 7.5, 0.6
wait_for_syringes
end_pressure_drop PT4, PT5  %   quit reading F3 pressure drop
% Sample to Desalt Filter transfer complete - release valves
close_valve SV1022         %   close 'Pump 1 - Desalt Isolation
                                   Valve-SV1022'
                                   (FIG. 8, valve 714)
sleep 1.0                  %   Pause 1 second
close_valve SV1026         %   close 'Pump 2-Desalt Isolation
                                   Valve-SV1026'
                                   (FIG. 8, valve 510)
% end Push Sample to Desalt Filter Routine
```

The above script may be stored in the local user interface 1605 and provided as the operational input 1615 to the controller 1330. The compiled software 1610 on the controller 1330 interprets the statements in the above script to generate commands or queries 1505 to/from components in the capillary electrophoresis circuit 1300 or valves, syringes, etc. in a preceding circuit, such as the denaturation circuit 900.

As described above, the compiled software 1610 includes software instructions unchangeable by the user. The compiled software 1610 interprets statements such as "open_valve SV1022" to mean "provide a signal to energize or deenergize the valve corresponding to the variable SV1022 in a manner such that the valve opens to allow a liquid source to flow into an inlet chamber." Responsively, the compiled software 1610 causes the controller(s) 701/1330 to produce signals that effect this instruction. Since the compiled software 1610 knows of the correspondence between the valve referred to as SV1022 in the operational input 1615 to correspond with, for example, valve 714 (FIG. 8), the user need only specify valve SV1022 to be sure that the correct valve, valve 714, will be opened. Similarly, valve SV1026 corresponds to valve 510 as shown in FIG. 8, so the "open valve SV1026" instruction will be interpreted as such by the compiled software 1610, which, in turn, causes the controller(s) 701/1330 to generate an electrical signal that energizes or de-energizes the valve 510 to produce the desired "open" state of the valve 510.

Continuing to refer to the script above, pressure sensors, whose addresses are known to the compiled software 1610 in connection with the variable names PT4 and PT5, are addressed by the controller 1330 executing the compiled software 1610 in response to receipt of the operational input 1615 that includes the 'watch_pressure_drop' statement. The addresses corresponding to the syringes SY1 and SY2 are also known to the compiled software 1610 and addressed by the controller(s) 701/1330 to "push" (i.e., deliver volume) and "pull" (i.e., acquire volume) in response to receipt of the 'start_syringe' statements listed above.

As should be understood from the above code, a "plain english" language set of programming instructions may be supported for a user of the system 1500 for customizing the process for collecting electrophoresis data 1620 from a sample of a processed macromolecule sample. The variable names (e.g., SV1022, SY1, PT4, etc.) may also be or include mnemonics or other forms of descriptors that are identified by the compiled software 1610 and represent corresponding devices or subsystems to be operated in a manner consistent with the command(s) associated therewith.

The correspondence information may be embedded directly in the code, stored as sets of constants or hard coded variables in the software, or stored in look-up table(s), list(s), such as arrays or linked lists, or calculations used by the controllers 701/1330 to determine the correspondence between the variable names and elements corresponding thereto.

In this way, once testing of the compiled software 1610 has been completed, where the testing typically includes an exhaustive set of test vectors that is consistent with a full range of possible inputs provided by users of the system 1500, the manufacturer, customer, and user of the system 1500 are assured that this correspondence is "fixed" such that inadvertent addressing errors by the controllers 701/1330 will not be encountered, excluding electronics errors or failures. In other words, operational input 1615 that includes commands listed above in the example script will result in a known and repeatable effect to ensure proper operation of the system 1500 for processing or analyzing macromolecules.

Figure 17:
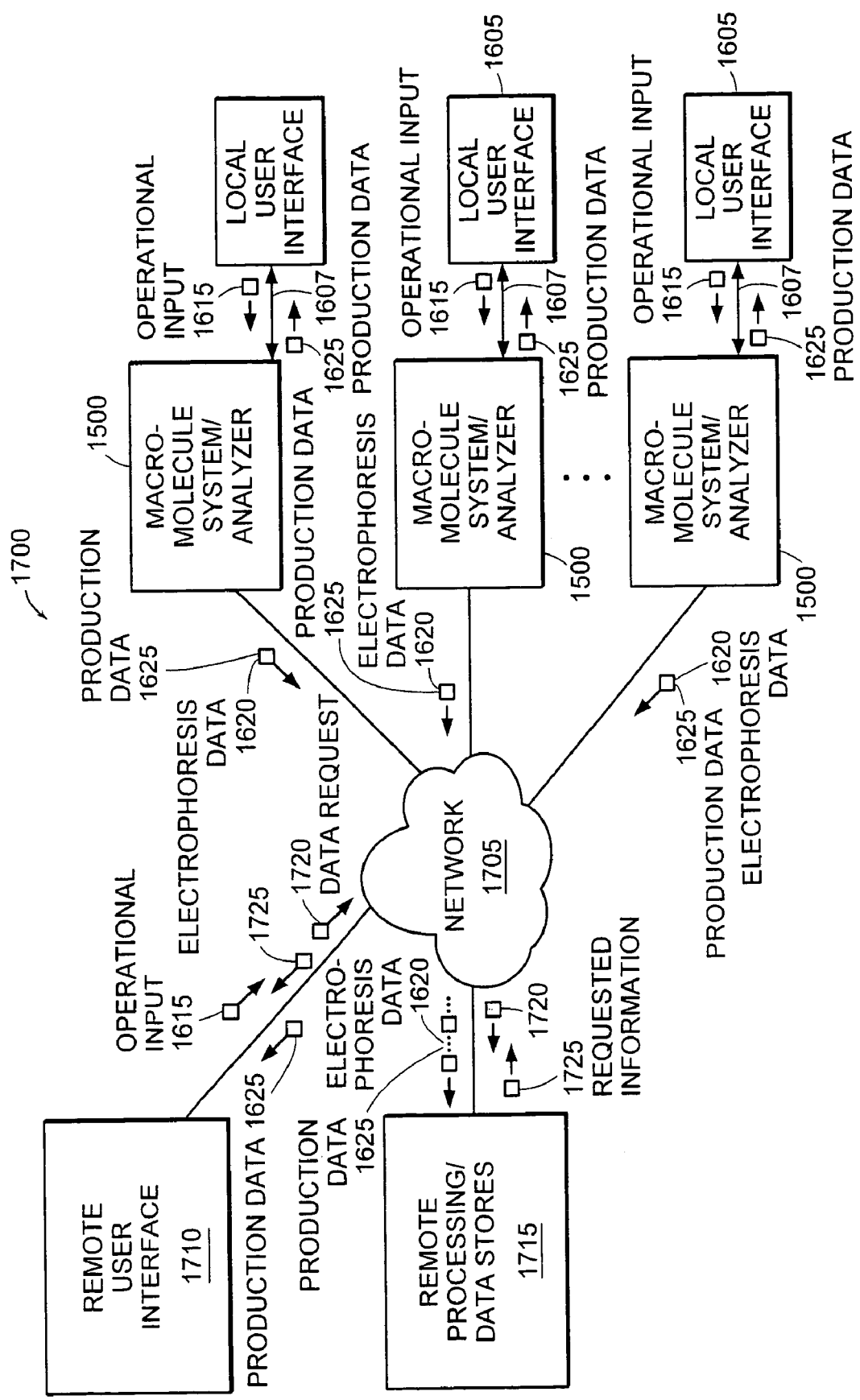
FIG. 17 is a network diagram including multiple systems of FIG. 16 connected to remote computing devices across a network.

FIG. 17 is a network diagram of a network 1700 that includes multiple macromolecule systems 1500 connected to a central or distributed network 1705. Each of the systems 1500 has a local user interface 1605, as described above in reference to FIG. 16. In this embodiment, however, the systems 1500 or local user interfaces 1605 include interfaces (not shown) to receive operational input 1615 from a remote user interface 1710 across the network 1705.

The remote user interface 1710 can be employed by a "central" operator to control or monitor a distributed network of the macromolecule systems 1500 for high yield production or analysis of macromolecules. For example, a large pharmaceutical company or manufacturer supplying biological product thereto may employ such a network for high volume production.

Beyond the operational inputs 1615, the remote user interface 1710 may also request data from a remote processing/data stores device 1715, which is also coupled to the network 1705 for interfacing with the systems 1500. The remote processing/data stores device 1715 may receive the production data 1625 or electrophoresis data 1620 for processing this data "off-line". For example, the remote processing/data stores device 1795 may determine yields or quality of the macromolecules processed by the systems 1500 and provide access to this data across the network 1705, for example, to the remote user interface 1710 or any of the local user interfaces 1605. Thus, in response to the data request 1720, the remote processing/data stores device 1715 may provide requested information 1725, including raw or processed data, across the network 1705 in a typical data exchange manner, such as through packetized communications.

It should be understood that the network 1705 may include various forms of communication networks, such as a Public Switched Telephone Network (PSTN), wired or Wireless Local Area Networks (WLAN's), cellular networks, circuit switching networks, Voice-Over-Internet-Protocol (VOIP) networks, and so forth.

It should be understood that the compiled software 1610 operating in the controllers 701/1330 of the systems 1500 may be organized into multiple software "units", such as a system control unit, network interface unit, local interface unit, and so forth. In this way, the compiled software 1610 can be updated with predetermined re-validation requirements to minimize future costs of maintaining the system 1500 by the customers.

Business Method

Figure 18:
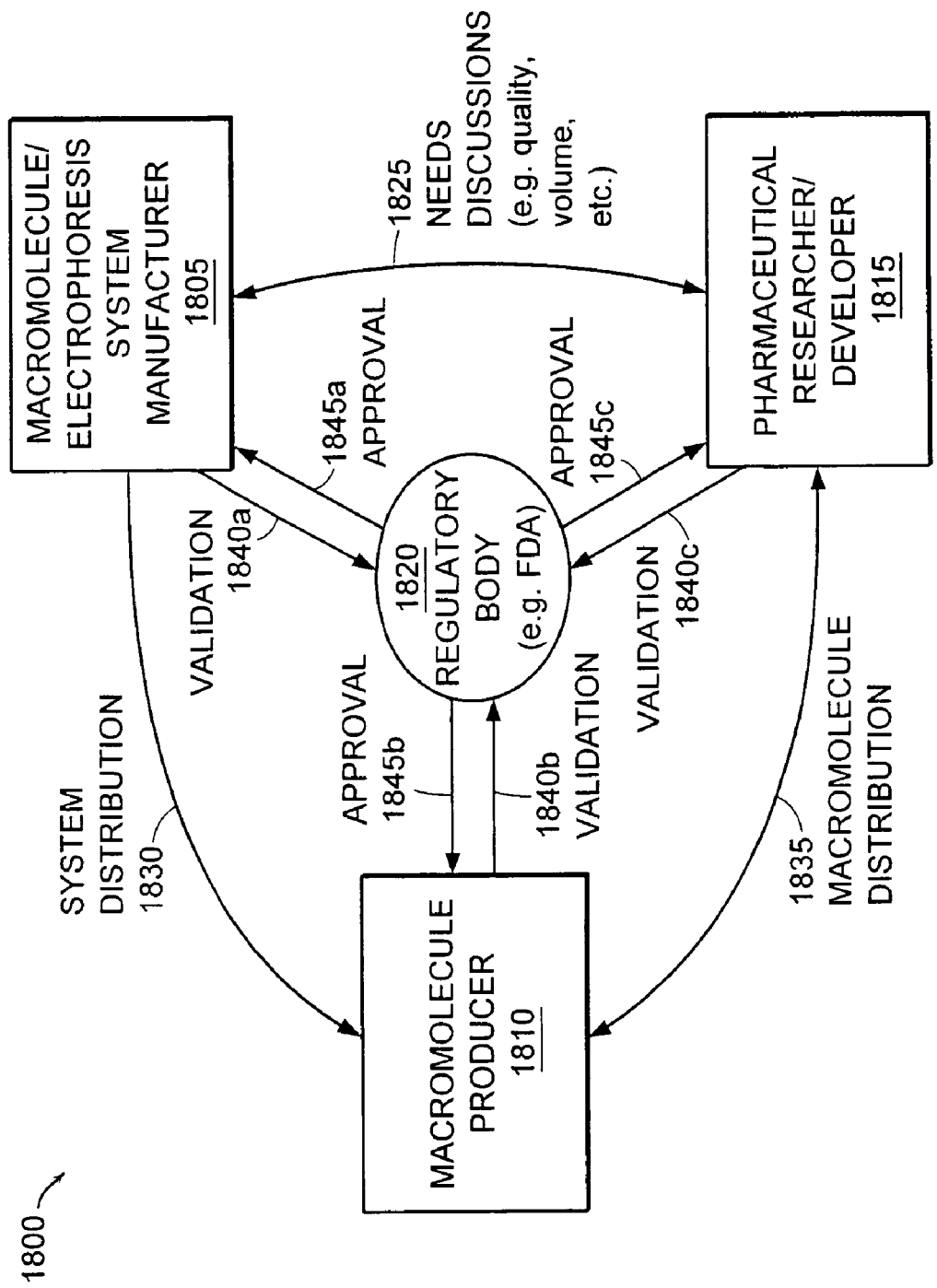
FIG. 18 is a block diagram of an industry model in which a business may distribute the system of FIG. 16.

FIG. 18 is a schematic diagram of a business model 1800 in which a manufacturer of systems subject to approval by a regulatory body 1820 operates. The regulatory body may (i) provide oversight of a system, such as the system 1600 discussed above, produced by the manufacturing company, (ii) provide oversight of the usage of the system, or (iii) provide oversight of products produced by the system. The user of the system and end user of products produced by the system may be the same or different companies or even the manufacturer of the system. By oversight, it is meant that the regulatory body may inspect (i) the system, (ii) usage of the system, or (iii) products produced by the system in a manner that protects workers operating the system or end users of the products produced by the system. As part of the oversight, the regulatory body may require validation of operation or end products of the system and, in turn, provide approval of the system based on the validation data provided by the manufacturer, user, or recipients of products of the system.

An example of a business model in which one or more companies operate under the auspices of a regulatory body is in the case of pharmaceutical material production. The regulatory body in this case is the Food and Drug Administration 1820. In this business model 1800, the FDA provides oversight to a manufacturer 1805 of a system for producing macromolecules and/or providing electrophoresis analysis of samples of the produced macromolecules. The FDA 1820 also oversees operation of the systems as used by a macromolecule producer 1810 (hereafter referred to as the producer 1810). Still further, the FDA 1820 oversees use of the macromolecules produced by the system 1500 by a pharmaceutical researcher/developer 1815 (hereafter referred to as researcher 1815).

In a typical business cycle, the manufacturer 1805 distributes systems (step 1830) to the producer 1810. The producer 1810 distributes materials (step 1835) produced through the use of the system to the researcher 1815. Prior to distribution of the systems and operation of the systems, the manufacturer 1805 may engage in discussions with the researcher 1815 (step 1825) to assess the needs of the researcher 1815, such as quality of the macromolecules, volume requirements for the macromolecules, and other production needs so as to design the system with those needs in mind to ensure commercialization of the systems.

Also included in the business model 1800 are validation and approval cycles (steps 1840, 1845) by each of the aforementioned companies. The validation and approval cycles 1840, 1845 may be required of each of the companies 1805, 1810, and 1815 for each of their respective parts in the business model 1800. For example, in the case of the macromolecule system 1600, before a system can be shipped by the manufacturer 1805, the FDA 1820 may require the manufacturer 1805 to participate in validation 1840a of the system (e.g., witness and verify data produced by the system, test results, or performance in response to test vectors provided to the system). After evaluation of validation data by the FDA 1820, the FDA 1820 may grant approval 1845*a* of the system. Following approval, the distribution of the system (step 1830) can occur, and shipment of the system may follow from the manufacturer 1805 to the producer 1810.

Similarly, the producer 1810 may have to provide data in the form of validation data to the FDA 1820 for approval 1845*b* before the system can be used by the producer 1810 to generate macromolecules, for example. The producer 1810 may have additional requirements for gaining approval 1845*b* from the FDA 1820. For example, the producer 1810 may have to customize operational input, as discussed above, to operate the system, and test results may have to be shown. In addition, actual macromolecules produced by the system may also have to be validated by the producer and sent to the FDA 1820 for approval to ensure quality of the macromolecules.

Similarly, the researcher 1815 may also have to send validation data to the FDA 1820 for approval 1840*c*. Typically, this validation and approval cycle 1840*c*, 1845*c* is for a drug or other pharmaceutical product produced by the system.

It should be understood that the regulatory body 1820 may be a government or non-government agency. For example, in addition to the FDA, the government agency may be the Department of Defense (DOD) that may be involved in the oversight of non-government entities to monitor systems, such as described above, for use in developing vaccines against toxic substances, such as anthrax, smallpox, and so forth.

Continuing to refer to the business model of FIG. 18, there may be a business advantage for the manufacturer 1805 to distibute a system 1500 that has minimal re-validation and re-approval of the system following development of operational input by the producer 1810 for its particular mode of operation. By limiting the amount of re-validation and re-approval of the system by the producer 1810, the producer 1810 is more likely to have shorter re-validation/re-approval cycles by the FDA 1820, which, ultimately, may lead to increased profits for the producer 1810 due to higher system usage and more distribution of systems by the manufacturer 1805 for this reason.

As discussed above in reference to FIGS. 16 and 17, one way to minimize exposure of the producer 1810 to re-validation/re-approval cycles 1840, 1845 is to provide executable instructions in the system 1500 that are unchangeable by the producer 1810. One way to make the executable instructions unchangeable is to provide it in a compiled form referred to hereafter as "compiled software" and deploy it in the system 1500, for example, in the form of software or firmware. The compiled software preferably conforms to a known industry standard, such as ANSI programming languages or standard protocols for interfacing with devices or subsystems used to operate the system 1600 (FIG. 16).

Figure 19:
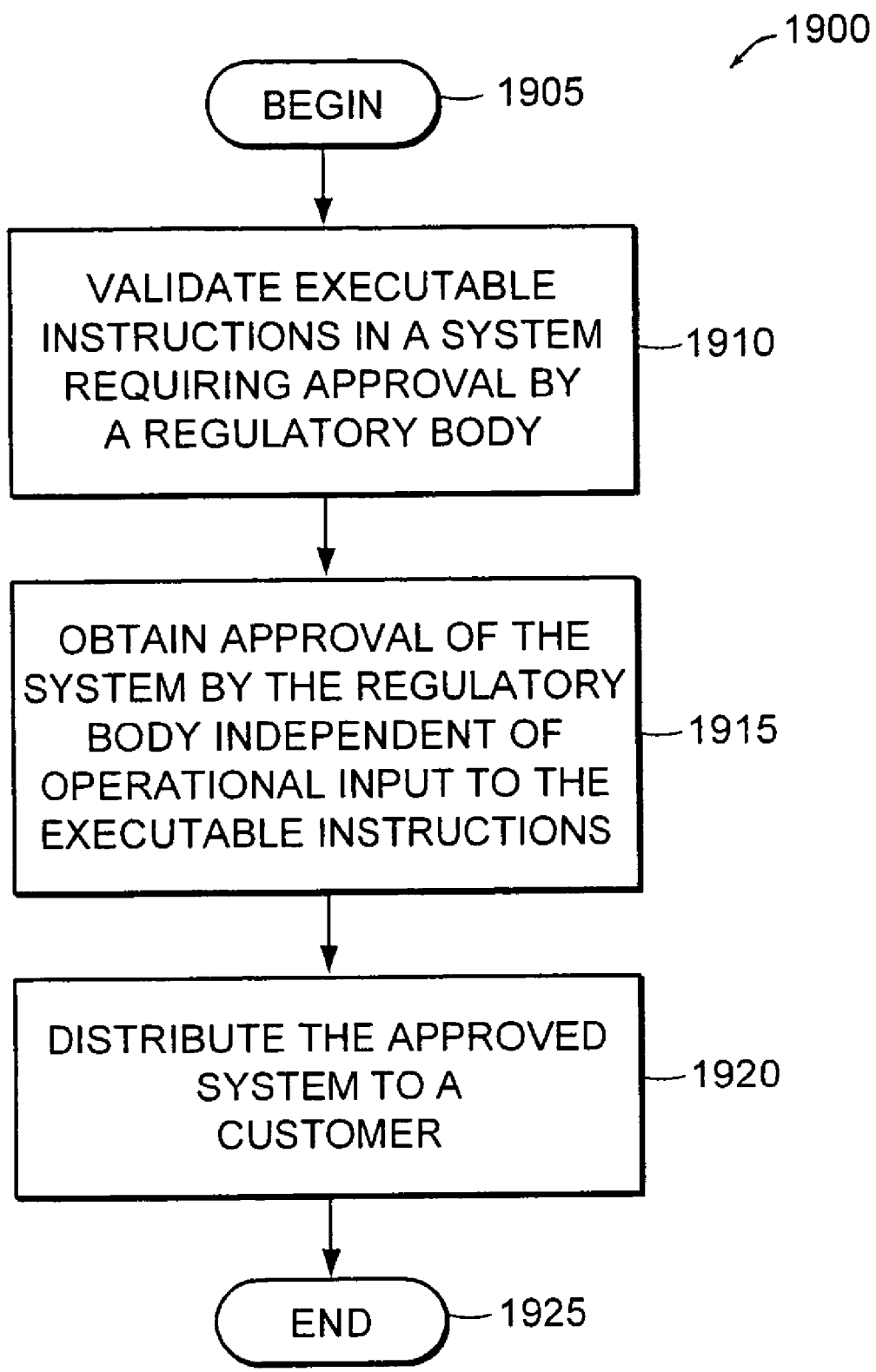
FIG. 19 is a generalized flow diagram of a business method used in the industry model of FIG. 18.
Figure 20:
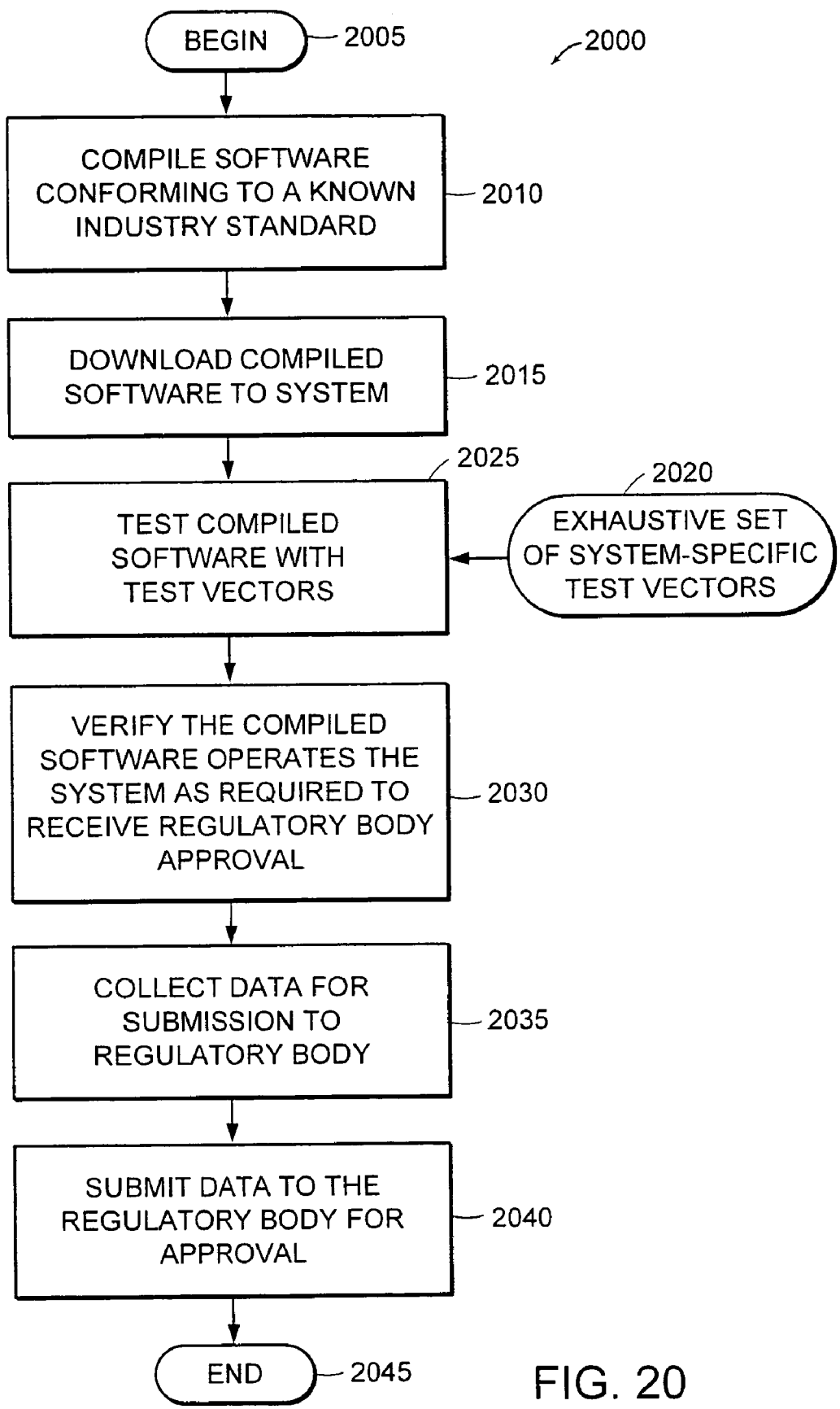
FIG. 20 is a flow diagram of a process used by the manufacturer of the system in FIG. 18.

A generalized flow diagram of the process just discussed is depicted in FIG. 19. In FIG. 19, a process 1900 is performed by the manufacturer of the system 1510. The process 1900 begins (step 1905) upon installation of compiled software in the system 1500. The manufacturer 1805 validates the compiled software in the system 1500 (step 1910), which requires approval by a regulatory body, such as the FDA 1820. The manufacturer 1805 obtains approval of the system 1500 by the regulatory body 1820 (step 1915) independent of operational input 1615 to the compiled software 1610. The manufacturer 1805 then distributes the approved system to a customer 1810 (step 1920). The process ends (step 1925) following distribution of the system 1500 (step 1830).

The process 1900 may involve additional steps for gaining validation 1840 and approval 1845 by the regulatory body 1820. For example, referring to FIG. 20, the manufacturer 1805 may have an internal process 2000 for performing the validation (step 1910). The internal process 2000 may begin (step 2005) at a point in which an employee of the manufacturer 1805 compiles software conforming to a known industry standard (step 2010). The employee then downloads the compiled software 1610 to the system (step 2015). In parallel, the same or another employee of the manufacturer 1805 may develop an exhaustive set of system-specific test vectors (step 2020) and use these test vectors to test the compiled software 1610 (step 2025). The employee verifies that the compiled software 1610 operates the system 1500 as required to receive the approval from the regulatory body 1820 (step 2030). During the verification (step 2030), the employee collects data for submission to the regulatory body 1820 (step 2035). The employee submits the data to the regulatory body 1820 for approval (step 2040), which completes the internal process 2000 (step 2045).

Figure 21:
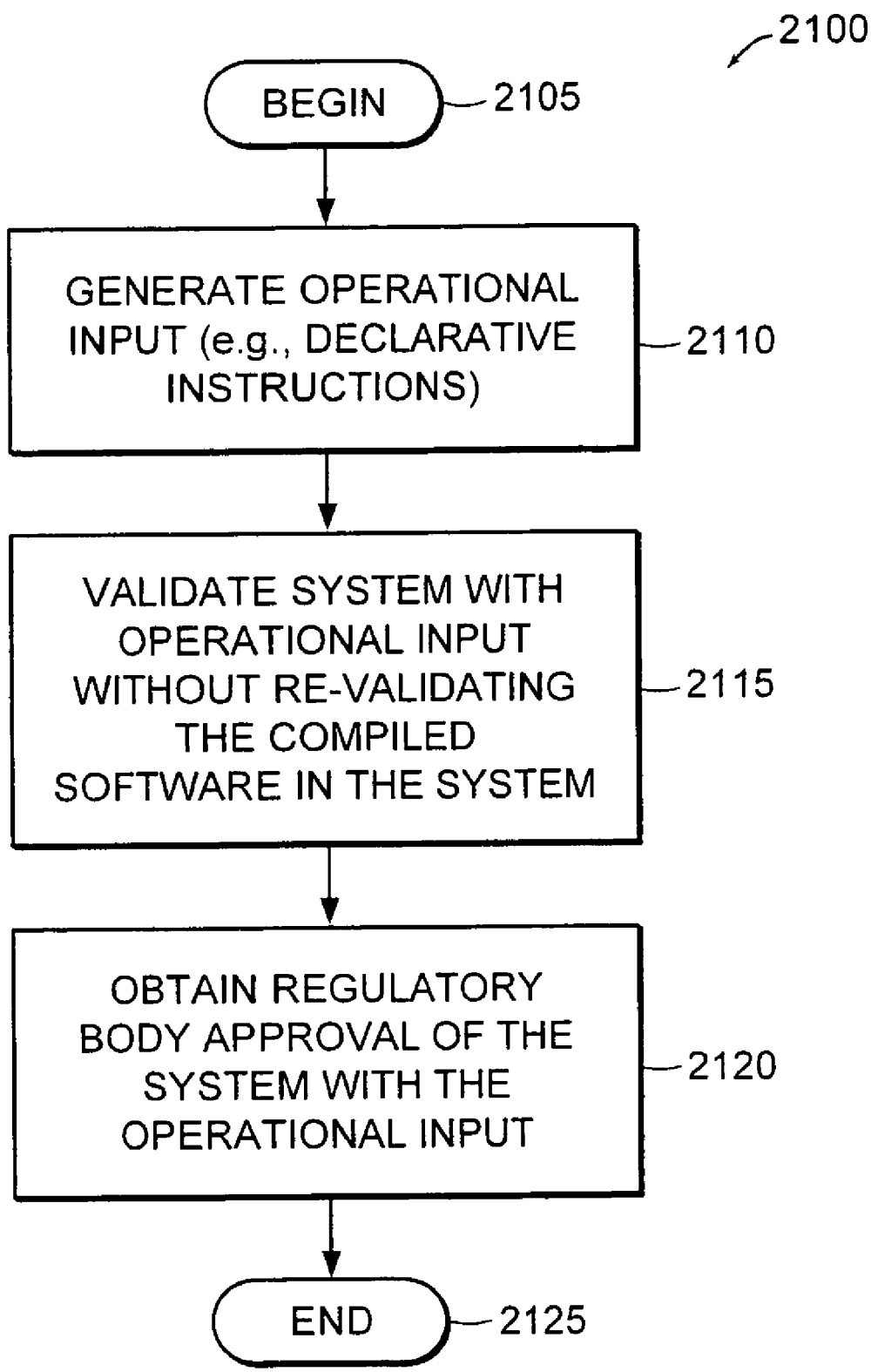
FIG. 21 is a flow diagram of a process used by a customer in FIG. 18.

Referring now to FIG. 21, from the point of view of the producer 1810, a separate process 2100 is conducted in which customization of the system 1500 is provided through custom design and use of operational input 1615. The process 2100 begins (step 2105) when the producer 1810 generates the operational input 1615 (e.g., declarative instructions) (step 2110). The producer 1810 validates the system (step 2115) with the operational input 1615 without having to re-validate the compiled software 1610 in the system 1500. The producer 1810 then seeks to obtain approval of the regulatory body 1820 for the system 1500 with the operational input 1615 (step 2120), which ends the process 2100 (step 2125).

Figure 22:
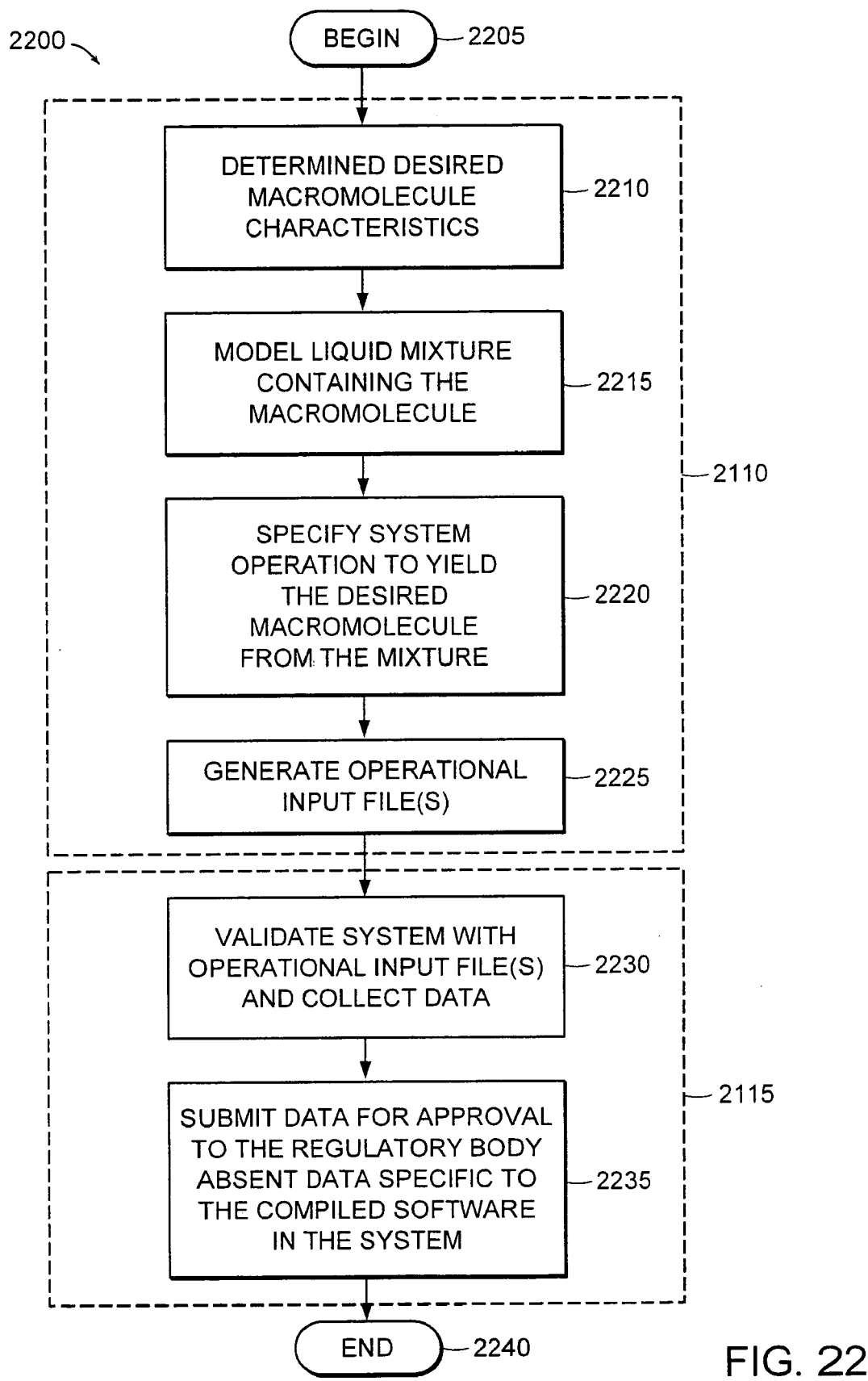
FIG. 22 is a detailed flow diagram of process steps in the flow diagram of FIG. 21.

The generation (step 2110) and validation (step 2115) of the operational input 1615 can include several substeps, which are shown in a process 2200 depicted in FIG. 22. The process 2200 begins (step 2205), and the producer 1810 generates (step 2110) the operational input 1615. A scientist or other employee of the macromolecule producer 1810 determines desired macromolecule characteristics (step 2210). The scientist or other employee models (step 2215) the liquid mixture 202 containing the macromolecule. The scientist or other employee specifies (step 2220) system 1500 operation to yield the desired macromolecule from the liquid mixture 202.

Based on the system specifications, the scientist or other employee generates at least one operational input file (file 2225). The validation (step 2115) begins following generation of the operational input file (step 2225). The scientist or other employee validates the system with the operational input file(s) and collects data corresponding thereto (step 2230). The producer 1810 submits the collected data for approval to the regulatory body 1820 absent data specific to the compiled software 1610 in the system 1500. In other words, at this time in the development cycle of the system 1500, the validation and approval cycle (steps 1840*b* and 1845*b*, respectively) do not include testing, data collection, and submission of the data corresponding to the compiled software 1610 because the compiled software 1610 has not changed in form or function since gaining approval 1845*a* by the manufacturer 1805 prior to the distribution 1830 of the system 1500. The process 2200 ends (step 2240), and the producer 1810 awaits approval 1845*b* from the regulatory body 1820.

For any number of reasons, the macromolecule producer 1810 may want to improve or modify the software in some way to improve the process provided by the system 1500 for either producing the macromolecules from the liquid mixture 202 or performing the electrophoresis analysis by the system 1500. In this case, all that the producer 1810 need modify is the operational input 1615 provided to the compiled software 1610 in the controllers 701/1330. In such a case, the producer 1810 can execute a different business process that is a subset of the business processes discussed above in reference to FIGS. 18–22.

Figure 23:
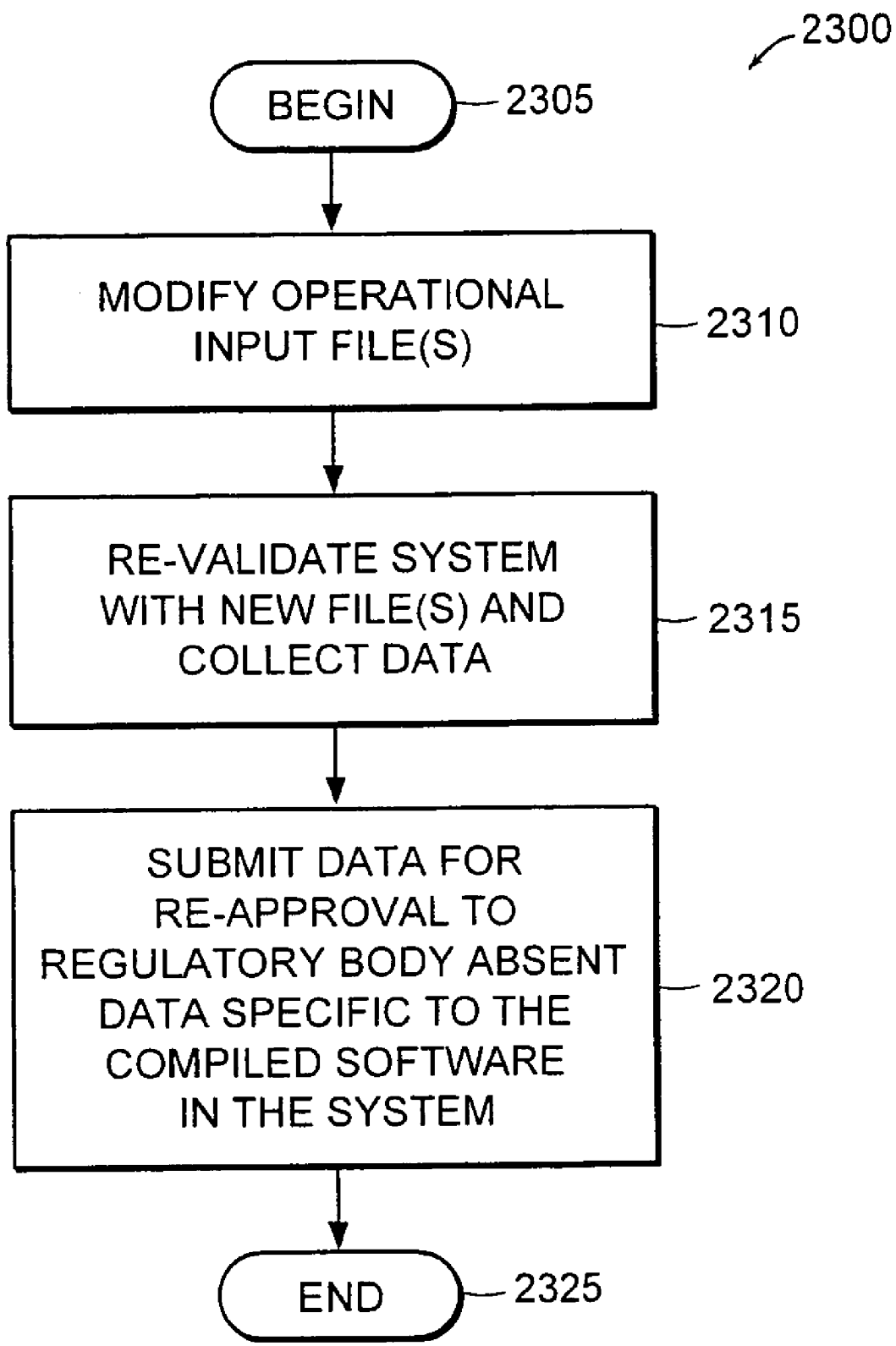
FIG. 23 is a flow diagram of a process also used by the customer in FIG. 18.

Referring now to FIG. 23, a business process 2300 executed by the producer 1810 begins (step 2305) upon a decision to change the process executed by the system 1600 for any number of reasons. A scientist or employee of the producer 1810 modifies the operational input file(s) (step 2310), causing a re-validation 1840b and re-approval 1845b of the system 1600 to be required by the regulatory body 1820. The re-validation is performed with the new file(s) and the employees collect data based on the operation of the system with the new operational input 1615 (step 2315). The producer 1810 submits the data to the regulatory body 1820 for re-approval absent data specific to the compiled software 1610 in the system 1500. Again, because the compiled software 1610 is unchangeable by the producer 1810 following its original validation and approval (steps 1840a and 1845a, respectively), the producer 1810 does not need to repeat these steps.

As used herein, a macromolecule can be a large molecule, typically a biological polymer that can be soluble in the liquid mixture. A macromolecule can be a protein or peptide, for example, a peptide hormone, an enzyme, an enzyme with an associated cofactor, an antibody, a glycoprotein, and the like. A macromolecule can be other biological polymers, for example, polysaccharides, e.g., starches or sugars, polynucleic acids, e.g., deoxyribonucleic (DNA) or ribonucleic acid (RNA), lipids, glycolipids, and the like. A macromolecule can also be other large molecules of interest, for example steroids, carbohydrates, organometallic complexes such as metalloporphyrins, and the like. A macromolecule can also be a non-biological molecule or polymer. A macromolecule can be two or more molecules that are associated through noncovalent interactions to form a complex, for example, an antibody-antigen complex, an enzyme-inhibitor complex, a multi-domain protein where the domains are linked by hydrophobic forces, and the like. Preferably, a macromolecule can be a biopolymer or other biological molecule that is the desired product of a particular bioreactor process. For example, in a bioreactor process designed to grow bacteria genetically engineered to express human insulin, the macromolecule is insulin. The macromolecule can also be a molecule that can be indicative of the desired product of a particular bioreactor process. Most preferably, a macromolecule is a protein. A macromolecule is typically between about 1,000 and about 200,000 atomic mass units (AMU) in molecular weight. Macromolecules are typically between about 10,000 and about 160,000 AMU.

As used herein, components that are smaller or larger than the macromolecule are those that can be separated from the macromolecule by filtration. Components that are smaller or larger than the macromolecule typically have a molecular weight that is greater or lesser than, respectively, the molecular weight of the macromolecule. One skilled in the art will know, however, that the relation of size to molecular weight for macromolecules and similar components is approximate and depends on a number of factors, including the actual molecular weight, the conformation of the molecule, whether the molecule is aggregated or agglomerated with other molecules, solvent conditions, ionic strength, filter composition, and the like.

As used herein, rough components can include soluble and insoluble components. Insoluble components include cells, fragments of cells, non-cellular tissue fragments, insoluble agglomerations of macromolecules, particulate contaminants, and the like. Soluble rough components include smaller fragments of cells, macromolecules that are larger than the macromolecule or are greater in molecular weight than the molecular weight of the macromolecule, and the like.

As used herein, fine components include soluble components. Soluble fine components include macromolecules that are smaller than the macromolecule or are lesser in molecular weight than the molecular weight of the macromolecule. Also included are small organic and inorganic molecules, for example, salts, amino acids, nucleic acids, cofactors, nutrients, metabolites, other macromolecules, fragments of the macromolecule, other biomolecules, and the like.

As used herein, salt components include salts formed from cations such as sodium, potassium, lithium, cesium, magnesium, manganese, copper, zinc, calcium, iron, ammonium, alkylammonium, phosphonium, sulfonium, and the like. Salt components also include anions including halides, sulfates, thiosulfates, sulfonates, sulfites, nitrates, nitrites, carboxylates, phosphates, phosphates, phosphonates, carbonates, hydroxides, and the like.

The liquid in the liquid mixture containing the macromolecule can be any solvent, for example, water, organic solvents such as alcohols, e.g., methanol, ethanol, isopropanol, t-butanol, and the like; ethers, e.g., dimethyl ether, diethyl ether, tetrahydrofuran, and the like; ketones, e.g., acetone, methyl ethyl ketone, and the like; aromatic solvents, e.g., benzene, toluene, and the like; halogenated solvents, e.g., chloroform, carbon tetrachloride, trichloroethylene, and the like; polar aprotic solvents, e.g., dimethyl sulfoxide, nitrobenzene, dimethyl formamide, n-methyl pyrrolidone, acetonitrile, and the like; mixtures thereof, and the like. Typically, the liquid can be water, optionally with small amounts of one or more organic solvents that are miscible with water, e.g., ethanol, isopropanol, acetonitrile, and the like.

As used herein, denaturation means changing the conformation and/or the solubility of a macromolecule to prepare it for analysis. For example, when macromolecule 104 in FIG. 4 is a protein, denaturation can include transformation from a packed three-dimensional conformation 104 to a linear conformation 104'. Denaturation can also include solubilizing the macromolecule with the denaturing detergent 220. Denaturation can be accomplished by techniques well known to one skilled in the art, for example, addition of one or more denaturation agents, application of heat, disulfide bond reduction, or a combination thereof. Denaturation agents for proteins can include, for example, chaotropic agents e.g., urea, guanidine hydrochloride, and the like; detergents, e.g. sodium dodecyl sulfate, potassium laurel sulfate, and the like; disulfide cleavage agents, e.g. dithiothreitol, dithioerythritol, and the like; acids or bases, e.g., trichloroacetic acid, sodium hydroxide, and the like; and other agents known to the art. Denaturation agents for polynucleic acids can include, for example, chelation agents, e.g. ethylenediamine tetraaceticacid and the like.

As used herein, a denaturation vessel can be any chamber or conduit where denaturation takes place, typically a small volume metal vessel, e.g., a stainless steel vessel between about 1 to about 100 mL. A denaturation vessel is typically coupled to a heating element, i.e., any device known to the art that can be used to heat the fluid mixture, for example, a resistive heating coil, a microwave heater, a combustion heater such as a gas flame, a heat pump, and the like. A denaturation vessel can also be coupled with a cooling element, for example, a heat pump, refrigeration unit, thermoelectric cooling element, radiator, water cooling coil, and the like. One skilled in the art will recognize that heating and cooling elements can be part of a single heat exchanger unit.

As used herein, a hydraulic system can be a collection of hydraulic conduits, one or more valves, and one or more pumps, coupled so that the pumps can be used to generate fluid pressure in the hydraulic lines and the valves can be controlled to direct the pressurized fluid through the lines. A pump can be any device known to the art that can be used to generate fluid flow, for example, an electro-kinetic pump, or a mechanical pump including a peristaltic pump, a syringe pump, an impeller pump, a pneumatic pump, and the like. A valve can be any device known to the art that can be used to control fluid flow, e.g., a needle valve, a gate valve, a butterfly valve, and the like. An automated controller can be a processor, e.g., an embedded processor, a desktop computer, and the like, that can be programmed to control a system adapted for automatic control, e.g., the hydraulic system.

As used herein, an ion concentration sensor can be any ion concentration sensor known to one skilled in the art, for example a general ion sensor such as a conductance sensor, or a specific ion sensor such as a chloride sensor, a hydrogen ion sensor (i.e., a pH sensor), and the like.

As used herein, a buffer can be any liquid that can be added to the mixture to maintain or change the concentration of a particular component, or to combine an additive to change the properties of the process. For example, an ionic buffer, e.g., a pH buffer, can change or maintain the pH of the liquid mixture; a denaturation buffer can contain a denaturation agent; a desalination buffer can be a liquid substantially free of salts or substantially free of a particular salt, e.g., sodium chloride; a lysis buffer can be a liquid that contains a lysing agent (e.g., a detergent) or can be sufficiently low in ionic strength to lyse cells by ionic shock; and the like. Lysing agents can include enzymes, e.g., L-lysine decarboxylase, lysostaphin, lysozyme, lyticase, mutanolysin, and the like. Lysing agents can include detergents, e.g. glycocholic acid sodium salt hydrate, lithium dodecyl sulfate, sodium cholate hydrate, sodium dodecyl sulfate, hexadecyltrimethylammonium bromide, N-Nonanoyl-N-methylglucamine, octyl-b-D-1-thioglucopyranoside, 3-(N,N-dimethyloctadecylammonio)propanesulfonate, and the like.

While this invention has been particularly shown and described with references to preferred embodiments thereof, it will be understood by those skilled in the art that various changes in form and details may be made therein without departing from the scope of the invention encompassed by the appended claims.

The following applications contain related subject matter and are incorporated herein by reference in their entirety; U.S. application Ser. No. 10/601,096 filed on Jun. 20, 2003, entitled "Method for Detection of Molecular species in a Crude Sample Using Capillary Electrophoresis," by Shin-Fuw Lin, et al., now abandoned; U.S. application Ser. No. 10/601,277 filed on Jun. 20, 2003, entitled "Automated Macromolecule Sample Preparation System," by George E. Barringer, Jr.; U.S. application Ser. No. 10/601,181 filed on Jun. 20, 2003, entitled "Stationary Capillary Electrophoresis System," by George E. Barringer, Jr.; and U.S. application Ser. No. 10/600,177 filed on Jun. 20, 2003, entitled "Method and Apparatus for Operating an Automated Biomolecular Preparation System," by George E. Barringer, Jr., et al.

What is claimed is:

1. A method of aseptically sampling a biofluid, comprising automatically:
    collecting a biofluid sample by opening an inlet valve at a biofluid source site;
    directing the sample through a trap to a biofluid process site by opening an outlet valve coupled to the process site, and closing a waste valve that couples the trap and a waste site, the trap being a portion of a sampling conduit extending from the inlet valve to the outlet valve, the trap having a low region that is lower than the inlet valve and the outlet valve, and the waste valve being coupled to the low region of the trap;
    isolating the biofluid sites by:
        closing the inlet and outlet valves; and
        opening the waste valve to drain biofluid from the trap to the waste site; and
    cleaning the sampling conduit before sample collection by directing a wash fluid through at least one valve selected from the inlet and outlet valves, and subsequently through the waste valve to the waste site.

2. The method of claim 1, further comprising cleaning before collecting each sample.

3. The method of claim 2, further comprising cleaning to reduce the number of bacterial colony forming units per milliliter of rinse water to less than about 100.

4. The method of claim 2, further comprising cleaning to reduce macromolecule contamination in rinse water to less than about 1 part per million.

5. The method of claim 2, further comprising cleaning by directing wash fluid through the outlet valve into the sampling conduit.

6. The method of claim 5, further comprising employing a wash fluid selected from steam, compressed air, an organic solvent, supercritical $CO_2$, and an aqueous cleaning solution.

7. The method of claim 6, further comprising directing the wash fluid through the inlet valve at the biofluid source site.

8. The method of claim 1, further comprising directing the wash fluid through a double isolated gate valve to the waste site, wherein at least one of the inlet and outlet valves is the double isolated gate valve, a waste output of each double isolated gate valve being coupled to the waste site.

9. The method of claim 8, wherein the inlet valve is a double isolated gate valve.

10. The method of claim 8, wherein the outlet valve is a double isolated gate valve.

11. The method of claim 1, further comprising monitoring for a backflow condition while the biofluid sites are isolated by sensing fluid flow.

12. The method of claim 11, further comprising sensing for fluid flow in the sampling conduit.

13. The method of claim 11, further comprising sensing for fluid flow through the waste valve.

14. The method of claim 11, further comprising isolating the biofluid sites by closing the waste valve and opening a relief valve that is located at a relief conduit, wherein the relief conduit has a proximal end coupled to the trap and a distal end coupled to the external environment.

15. The method of claim 14, further comprising sensing for fluid flow in the relief conduit.

16. The method of claim 15, further comprising excluding particulate contaminants from entering the relief conduit by employing a filter selected to remove particulates having a diameter of at least about 0.2 µm.

17. The method of claim 16, further comprising collecting overflowing biofluid in an overflow reservoir at the relief conduit.

18. The method of claim 1, further comprising locating the inlet and outlet valves at the same height.

19. The method of claim 18, further comprising draining biofluid from the trap at a location that is lower than the inlet and the outlet valves by a least about 3 times the inside diameter of the conduit.

20. The method of claim 19, further comprising draining biofluid from the lowest point of the trap.

21. A method of aseptically sampling a biofluid, comprising automatically:
   collecting a biofluid sample by opening an inlet valve at a biofluid source site;
   directing the sample to a biofluid process site by:
   opening an outlet valve, coupled to to process site, that is located at the same height as the inlet valve;
   closing a waste valve that couples a trap and a waste site, the trap being a portion of a sampling conduit extending front the inlet valve to the outlet valve, the trap having a low region that is lower than the inlet and outlet valve, and the waste valve being coupled to the low region of to trap;
   isolating the biofluid sites by:
      closing the inlet and outlet valves;
      opening the waste valve to drain biofluid from the trap to the waste site;
      closing the waste valve and opening a relief valve located at a relief conduit, the relief conduit having a proximal end coupled to the trap and a distal end coupled to a filter selected to exclude particulate contaminants having a diameter of at least about 0.2 µm; and
   monitoring for backflow by sensing fluid flow in the relief conduit; and cleaning the sampling conduit before collecting each sample, including:
      directing a wash fluid through the outlet valve, into to sampling conduit, and through the waste valve to the waste site; and
      reducing macromolecule contamination in the sampling conduit to less than about 1 part per million.

22. A method of aseptically sampling a biofluid, comprising automatically:
   collecting a biofluid sample by opening an inlet valve at a biofluid source site;
   directing the sample to a biofluid process site by opening an outlet valve coupled to to process site, and closing a waste valve that couples a trap and a waste site, wherein the trap is located at a sampling conduit extending from the inlet valve to the outlet valve;
   isolating the biofluid sites by:
      closing the inlet and outlet valves; and
      opening the waste valve to drain biofluid from the trap to the waste site; and
   cleaning the sampling conduit before sample collection by directing a wash fluid through a double isolated gate valve to the waste site, at least one of the inlet and outlet valves being the double isolated gate valve, an output of each double isolated gate valve being coupled to the waste site, through at least one valve selected from the inlet and outlet valves, and subsequently through the waste valve to the waste site, the wash fluid selected from steam, compressed air, an organic solvent, supercritical $CO_2$, and an aqueous cleaning solution.

23. The method of claim 22, wherein the inlet valve is a double isolated gate valve.

24. The method of claim 22, wherein the outlet valve is a double isolated gate valve.

* * * * *

UNITED STATES PATENT AND TRADEMARK OFFICE
CERTIFICATE OF CORRECTION

PATENT NO.        : 7,169,599 B2                                              Page 1 of 1
APPLICATION NO.   : 10/601083
DATED             : January 30, 2007
INVENTOR(S)       : George E. Barringer, Jr.

It is certified that error appears in the above-identified patent and that said Letters Patent is hereby corrected as shown below:

Column 27

Line 17, delete "coupled to to" and insert --coupled to the--.

Signed and Sealed this

Twenty-sixth Day of February, 2008

JON W. DUDAS
*Director of the United States Patent and Trademark Office*